(12) United States Patent
Takahashi et al.

(10) Patent No.: US 9,814,399 B2
(45) Date of Patent: Nov. 14, 2017

(54) BIOLOGICAL INFORMATION DETECTION APPARATUS

(71) Applicant: Seiko Epson Corporation, Shinjuku-ku (JP)

(72) Inventors: Yusuke Takahashi, Matsumoto (JP); Hideto Yamashita, Suwa (JP); Masao Kuroda, Shiojiri (JP); Ichiro Aoshima, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 406 days.

(21) Appl. No.: 14/205,154

(22) Filed: Mar. 11, 2014

(65) Prior Publication Data
US 2014/0276116 A1 Sep. 18, 2014

(30) Foreign Application Priority Data

Mar. 18, 2013 (JP) .................. 2013-054490
Mar. 18, 2013 (JP) .................. 2013-054491

(51) Int. Cl.
*A61B 5/02* (2006.01)
*A61B 5/024* (2006.01)
*A61B 5/00* (2006.01)

(52) U.S. Cl.
CPC ...... *A61B 5/02427* (2013.01); *A61B 5/02416* (2013.01); *A61B 5/681* (2013.01)

(58) Field of Classification Search
None
See application file for complete search history.

(56) References Cited

U.S. PATENT DOCUMENTS

| 5,766,131 A | 6/1998 | Kondo et al. |
| 6,605,045 B2 | 8/2003 | Ohsaki et al. |

(Continued)

FOREIGN PATENT DOCUMENTS

| EP | 0 756 849 A1 | 2/1997 |
| EP | 0 941 694 A1 | 9/1999 |

(Continued)

OTHER PUBLICATIONS

Extended European search report, dated May 20, 2014, of the corresponding European Application No. 14159850.8.

(Continued)

*Primary Examiner* — Eric Winakur
*Assistant Examiner* — Marjan Fardanesh
(74) *Attorney, Agent, or Firm* — Kilpatrick Townsend & Stockton LLP

(57) ABSTRACT

A biological information detection apparatus includes a detection unit which has a light receiving unit receiving light from a subject, a light transmitting member which is provided on a housing surface side in contact with the subject of the biological information detection apparatus, transmits light from the subject, and comes into contact with the subject when measuring biological information of the subject, and a diaphragm unit which is provided between the light transmitting member and the detection unit, between the light transmitting member and the subject, or inside the light transmitting member, and narrows light from the subject in an optical path between the subject and the detection unit. The detection unit includes a light emitting unit which emits light to the subject, and the biological information detection apparatus has a light shielding unit which is provided between the light receiving unit and the light emitting unit.

18 Claims, 19 Drawing Sheets

(56) References Cited

U.S. PATENT DOCUMENTS

| | | |
|---|---|---|
| 2004/0062056 A1 | 4/2004 | Heine et al. |
| 2007/0270702 A1 | 11/2007 | Ahola |
| 2008/0144004 A1* | 6/2008 | Rosenthal ............ G01N 21/359 356/39 |
| 2011/0092832 A1 | 4/2011 | Onoe et al. |
| 2011/0166457 A1 | 7/2011 | Sato et al. |
| 2011/0260176 A1 | 10/2011 | Onoe et al. |
| 2013/0267854 A1* | 10/2013 | Johnson ............... A61B 5/0082 600/473 |

FOREIGN PATENT DOCUMENTS

| | | |
|---|---|---|
| EP | 1 447 044 A1 | 8/2004 |
| EP | 2 020 202 A2 | 2/2009 |
| EP | 2 020 202 A3 | 2/2009 |
| EP | 2 520 222 A1 | 11/2012 |
| JP | 57-093039 A | 6/1982 |
| JP | 2001-353133 A | 12/2001 |
| JP | 2004-188224 A | 7/2004 |
| JP | 2005-270543 A | 10/2005 |
| JP | 2008-043515 A | 2/2008 |
| JP | 2008-086705 A | 4/2008 |
| JP | 2008-237453 A | 10/2008 |
| JP | 2009-006070 A | 1/2009 |
| JP | 2009-200433 A | 9/2009 |
| JP | 2009-201919 A | 9/2009 |
| JP | 2011-39725 A | 7/2011 |
| JP | 5031894 B2 | 7/2012 |
| TW | 200 722 047 A | 6/2007 |
| WO | 2009/139029 A1 | 11/2009 |

OTHER PUBLICATIONS

European search report, dated May 28, 2014, of the corresponding European Application No. 14159853.2. 6 pgs.

Extended European search report, dated Sep. 23, 2014, of the corresponding European Application No. 14159853.2. 14 pgs.

* cited by examiner

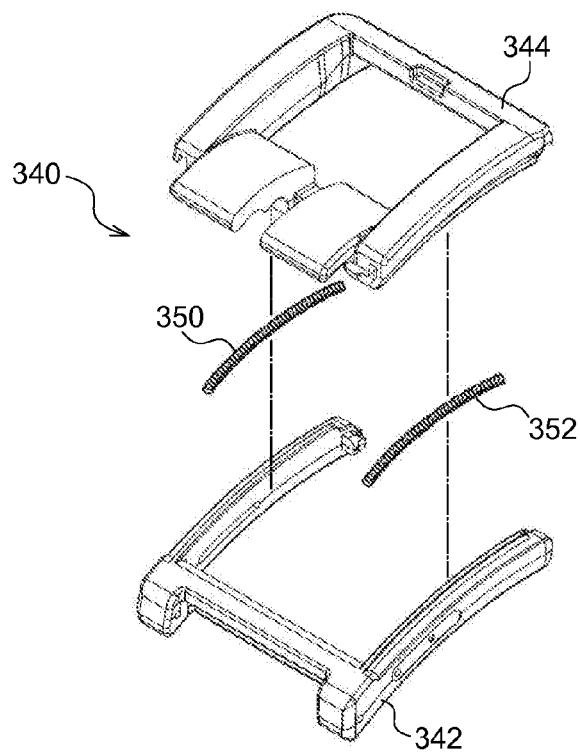
FIG. 2A
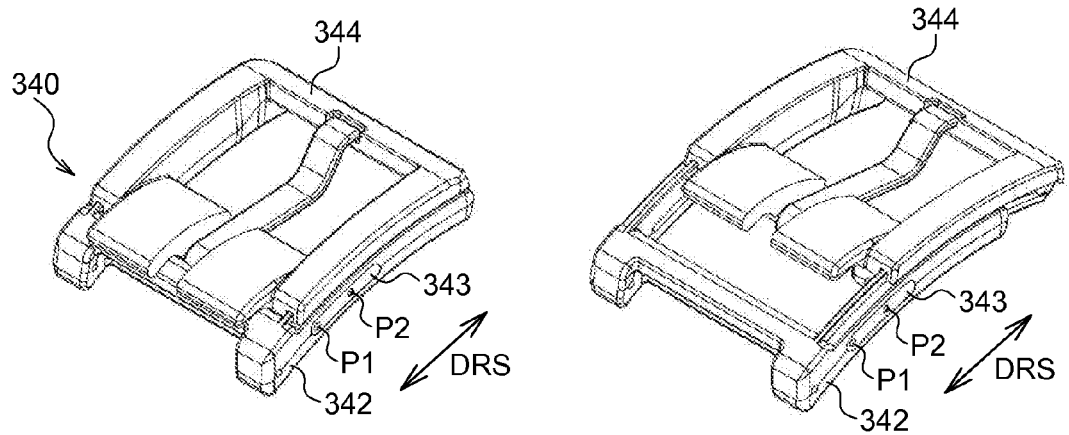
FIG. 2B                    FIG. 2C

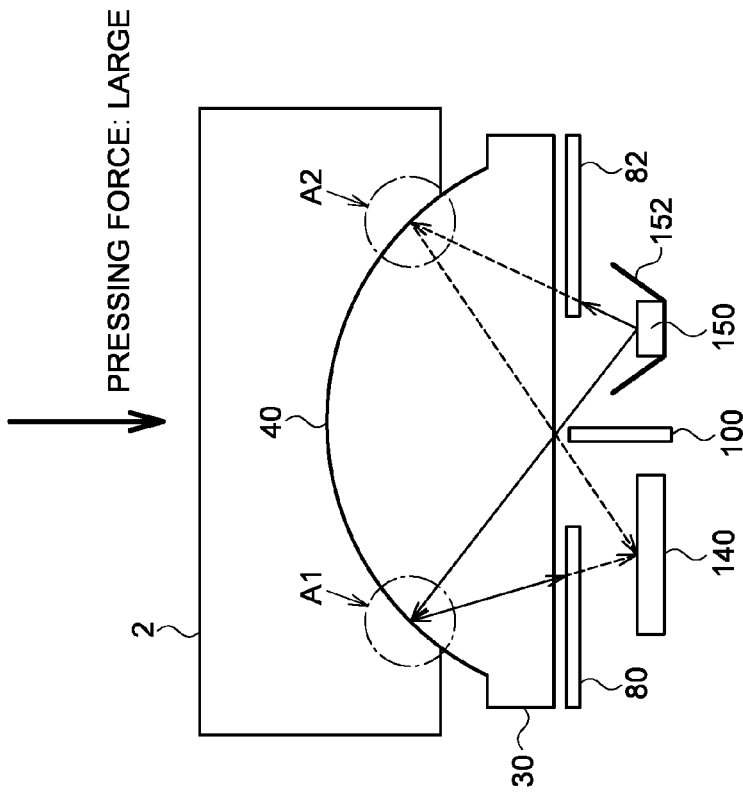
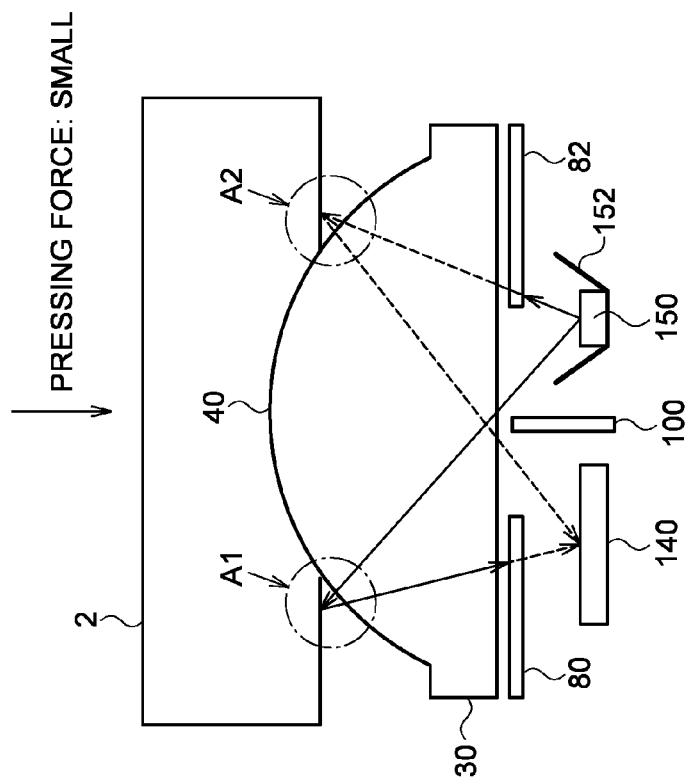

BIOLOGICAL INFORMATION DETECTION APPARATUS

CROSS-REFERENCE TO RELATED APPLICATION

The present application is based on and claims priority from Japanese Patent Application No. 2013-054490, filed Mar. 18, 2013, and Japanese Patent Application No. 2013-054491, filed Mar. 18, 2013, the disclosures of which are incorporated by reference herein.

BACKGROUND

1. Technical Field

The present invention relates to a biological information detection apparatus and the like.

2. Related Art

A biological information detection apparatus which detects biological information, such as a pulse wave of a human, is hitherto known. JP-A-2011-139725 and JP-A-2009-201919 disclose a pulsimeter of the related art which is an example of the biological information detection apparatus. The pulsimeter is put on, for example, an arm, a wrist, a finger, or the like, and detects pulsation resulting from heartbeat of a human body to measure a pulse rate.

The pulsimeter disclosed in JP-A-2011-139725 and JP-A-2009-201919 is a photoelectric pulsimeter, and a detection unit (pulse wave sensor) of the pulsimeter has a light emitting unit which emits light toward a subject (a region to be detected), and a light receiving unit which receives light (light having biological information) from the subject. In this pulsimeter, change in blood flow is detected as change in the amount of received light, thereby detecting a pulse wave. JP-A-2011-139725 discloses a pulsimeter which is put on a wrist, and JP-A-2009-201919 discloses a pulsimeter which is put on a finger.

In JP-A-2011-139725 and JP-A-2009-201919, a light transmitting member which transmits light from the light emitting unit or light from the subject is provided, and the light transmitting member has a contact surface with the subject (the skin of the wrist or the finger). Then, change in the contact state of the contact surface with the subject causes degradation of signal quality of a detection signal of the biological information, and degradation of reliability, detection precision, or the like of the biological information. If direct light from the light emitting unit enters the light receiving unit, reliability, detection precision, or the like of the biological information is further degraded.

SUMMARY

An aspect of the invention relates to a biological information detection apparatus including a detection unit which has a light receiving unit receiving light from a subject, a light transmitting member which is provided on a housing surface side in contact with the subject of the biological information detection apparatus, transmits light from the subject, and comes into contact with the subject when measuring biological information of the subject, and a diaphragm unit which is provided between the light transmitting member and the detection unit, between the light transmitting member and the subject, or inside the light transmitting member, and narrows light from the subject in an optical path between the subject and the detection unit.

BRIEF DESCRIPTION OF THE DRAWINGS

The invention will be described with reference to the accompanying drawings, wherein like numbers reference like elements.

FIGS. 2A to 2C are explanatory views of a connection of the biological information detection apparatus.

FIGS. 7A and 7B are explanatory views of a method of this embodiment.

DESCRIPTION OF EXEMPLARY EMBODIMENTS

Figure 1A:
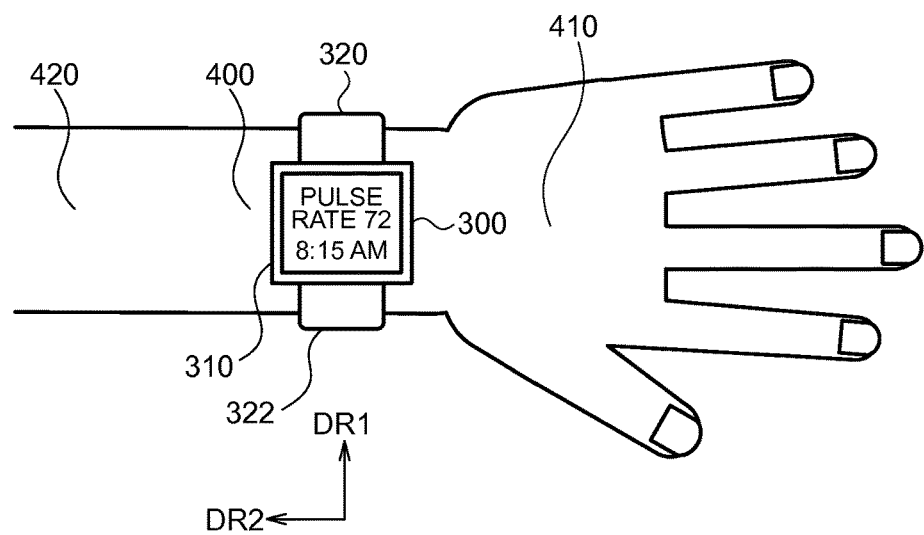
FIGS. 1A and 1B are appearance diagrams of a biological information detection apparatus of this embodiment.

According to a few aspects of the invention, it is possible to provide a biological information detection apparatus or the like which can detect appropriate biological information even when there is change in a contact state of a contact surface with a subject, or the like.

A biological information detection apparatus according to an embodiment of the invention includes a detection unit which has a light receiving unit receiving light from a subject, a light transmitting member which is provided on a housing surface side in contact with the subject of the biological information detection apparatus, transmits light from the subject, and comes into contact with the subject when measuring biological information of the subject, and a diaphragm unit which is provided between the light transmitting member and the detection unit, between the light transmitting member and the subject, or inside the light transmitting member, and narrows light from the subject in an optical path between the subject and the detection unit.

According to this embodiment, the light transmitting member comes into contact with the subject when measuring the biological information of the subject, and light passing through the light transmitting member is received by the light receiving unit of the detection unit, thereby detecting the biological information of the subject. In this embodiment, the diaphragm unit is provided to narrow light from the subject in the optical path between the subject and the detection unit. With this configuration, even when stray light occurs due to change in the contact state of the contact surface with the subject or the like, it is possible to suppress the entrance of stray light to the light receiving unit, and to detect appropriate biological information.

In this embodiment, the detection unit may include a light emitting unit which emits light to the subject, the light transmitting member may transmit light from the light emitting unit, and the diaphragm unit may narrow light from the light emitting unit in the optical path between the subject and the detection unit.

With this configuration, it is possible to suppress a situation in which light from the light emitting unit becomes stray light, and appropriate biological information cannot be detected.

In this embodiment, the diaphragm unit may include a first diaphragm unit provided on the light receiving unit side and a second diaphragm unit provided on the light emitting unit side.

With this configuration, it becomes possible to suppress the entrance of stray light to the light receiving unit using, for example, the first diaphragm unit, or to suppress light from the light emitting unit from becoming stray light using, for example, the second diaphragm unit.

In this embodiment, the area of an opening of the second diaphragm unit provided on the light emitting unit side may be smaller than the area of an opening of the first diaphragm unit provided on the light receiving unit side.

With this configuration, the area of the opening of each of the first and second diaphragm units can be set to the area suitable for improving optical efficiency or performance, improving product yield, or the like.

In this embodiment, the biological information detection apparatus may further include a light shielding unit which is provided between the light receiving unit and the light emitting unit.

With this configuration, it becomes possible to suppress adverse effects due to the contact state of the contact surface with the subject or the like using the diaphragm unit, and to suppress adverse effects due to direct light from the light emitting unit using the light shielding unit. Accordingly, it is possible to provide a biological information detection apparatus which can detect appropriate biological information.

In this embodiment, when the height of the light shielding unit in a direction orthogonal to the housing surface is H1, and the height of a lower surface which is the surface of the diaphragm unit on the detection unit side is H2, H1>H2.

With this configuration, for example, it is possible to suppress a situation in which light from the light emitting unit is reflected by the diaphragm unit or the like and enters the light receiving unit.

In this embodiment, the diaphragm unit and the light shielding unit may be formed integrally as a light shielding member.

The light shielding member formed integrally is used, whereby, for example, it becomes possible to complement a lack of strength in, for example, the light shielding unit or the like, or to share a material between the diaphragm unit and the light shielding unit.

In this embodiment, the light shielding member may be attached to a substrate, on which the light receiving unit and the light emitting unit are mounted, from the top of the substrate.

With this configuration, the light shielding member is attached to the substrate on which the light receiving unit and the light emitting unit are mounted, since it is possible to complete assembling of a sensor portion having the diaphragm unit, the light shielding unit, the light receiving unit, and the light emitting unit, it is possible to improve ease of assembling when manufacturing or the like.

In this embodiment, the light shielding unit may be a light shielding wall which is formed to extend in a direction orthogonal to the housing surface.

With the use of the light shielding wall, it is possible to effectively suppress the entrance of direct light from the light emitting unit to the light receiving unit.

In this embodiment, the width of the light shielding wall may be thinned toward a line connecting the light receiving unit and the light emitting unit.

With this configuration, it becomes possible to bring the light receiving unit and the light emitting unit close to each other in a region where the width of the light shielding wall is thin, thereby achieving improvement of optical efficiency or performance or the like.

In this embodiment, when the angle between a line, which connects a first end portion of a light transmitting region of the light transmitting member and a second end portion as an end portion away from the first end portion of the light transmitting region out of two end portions of the light receiving unit, and the optical axis of the light receiving unit is θr, and the angle between a line, which connects the second end portion of the light receiving unit and an end portion on an opening side of the diaphragm unit, and the optical axis is θa, θa<θr.

In this way, if the relationship of θa<θr is established, for example, it becomes possible to allow light from the first end portion of the light transmitting region of the light transmitting member to be shielded by the diaphragm unit so as not to enter the light receiving unit.

In this embodiment, the diaphragm unit may be arranged and set such that the diaphragm unit is located on a line, which connects a first end portion of a light transmitting region of the light transmitting member and a first end portion as an end portion close to the first end portion of the light transmitting region out of two end portions of the light receiving unit, and a line, which connects a second end portion of the light transmitting region of the light transmitting member and a second end portion as an end portion close to the second end portion of the light transmitting region out of the two end portions of the light receiving unit.

With this configuration, it is possible to ensure that stray light from the first and second end portions of the light transmitting member is shielded by the diaphragm unit.

In this embodiment, when the angle between a line, which connects a second end portion of a light transmitting region of the light transmitting member and a first end portion as an end portion away from the second end portion of the light transmitting region out of two end portions of the light emitting unit, and the optical axis of the light emitting unit is θt, and the angle between a line, which connects the first end portion of the light emitting unit and an end portion on an opening side of the diaphragm unit, and the optical axis is θb, θb<θt.

In this way, if the relationship of θb<θt is established, for example, it is possible to allow light from the light emitting unit toward the second end portion of the light transmitting region of the light transmitting member to be shielded by the diaphragm unit or the like, thereby detecting appropriate biological information.

In this embodiment, the diaphragm unit may be arranged and set such that the diaphragm unit is located on a line, which connects a first end portion of a light transmitting region of the light transmitting member and a first end portion as an end portion close to the first end portion of the light transmitting region out of two end portions of the light emitting unit, and a line, which connects a second end portion of the light transmitting region of the light transmitting member and a second end portion as an end portion close to the second end portion of the light transmitting region out of the two end portions of the light emitting unit.

With this configuration, it is possible to ensure that light from the light emitting unit toward the first and second end portions of the light transmitting region of the light transmitting member is shielded by the diaphragm unit.

In this embodiment, the area of a diaphragm region of the diaphragm unit may be smaller than the area of a light transmitting region of the light transmitting member.

With this configuration, it becomes possible to allow light passing through a predetermined region of the light transmitting member to be shielded by the diaphragm unit.

In this embodiment, the diaphragm unit may shield light passing through a marginal region of the light transmitting member.

With this configuration, it is possible to suppress a situation in which appropriate biological information cannot be detected due to light passing through the marginal region of the light transmitting member.

In this embodiment, the light transmitting member may have a convex portion which comes into contact with the subject when measuring the biological information of the subject and gives a pressing force, and the diaphragm unit shields light passing through the marginal region of the convex portion.

With this configuration, when the convex portion for giving an appropriate pressing force to the subject is provided for the light transmitting member, it is possible to suppress a situation in which appropriate biological information cannot be detected due to light passing through the marginal region of the convex portion.

In this embodiment, the biological information detection apparatus may further include a pressing force suppression unit which is disposed in periphery of the convex portion, and suppresses the pressing force given to the subject by the convex portion.

With this configuration, the pressing force given to the subject by the convex portion is suppressed by the pressing force suppression unit, making it possible to reduce change in pressing force.

In this embodiment, when the amount of change in pressing force of the convex portion with respect to a load by a load mechanism generating the pressing force of the convex portion is defined as the amount of change in pressing force, the pressing force suppression unit may suppress the pressing force given to the subject by the convex portion such that the amount of change in pressing force in a second load range in which the load of the load mechanism is greater than FL1 becomes smaller than the amount of change in pressing force in a first load range in which the load of the load mechanism is 0 to FL1.

With this configuration, the pressing force given to the subject by the convex portion is suppressed by the pressing force suppression unit while giving an appropriate initial pressing force to the subject by the convex portion, making it possible to reduce change in pressing force or the like.

In this embodiment, the diaphragm unit may be provided between the light transmitting member and the detection unit.

However, the arrangement and setting of the diaphragm unit is not limited to such arrangement and setting.

In this embodiment, the shape of a diaphragm region of the diaphragm unit may be similar to the shape of a light transmitting region of the light transmitting member.

In this embodiment, a pulse wave may be detected as the biological information.

However, the biological information to be detected by the biological information detection apparatus is not limited to the pulse wave.

Hereinafter, this embodiment will be described. This embodiment described below is not unduly limited to the disclosure of the invention described in the appended claims. All configurations described in this embodiment are not necessarily the essential components of the invention.

1. Biological Information Detection Apparatus

FIG. 1A is an appearance diagram showing an example of a biological information detection apparatus (biological information measuring apparatus) of this embodiment. The biological information detection apparatus is a timepiece type pulsimeter, and has a main body 300 and bands 320 and 322 (wrist bands) for attaching the biological information detection apparatus to a wrist 400 of the subject. The main body 300 as an apparatus main body is provided with a display unit 310 which displays various kinds of information, a pulse wave sensor (a sensor having a detection unit, a light transmitting member, and the like), a processing unit which performs various kinds of processing, and the like. The measured pulse rate or time is displayed on the display unit 310. In FIG. 1A, a circumferential direction of the wrist 400 (or an arm) is defined as a first direction DR1, and a direction from a hand 410 to a lower arm 420 is defined as a second direction DR2.

Figure 1B:
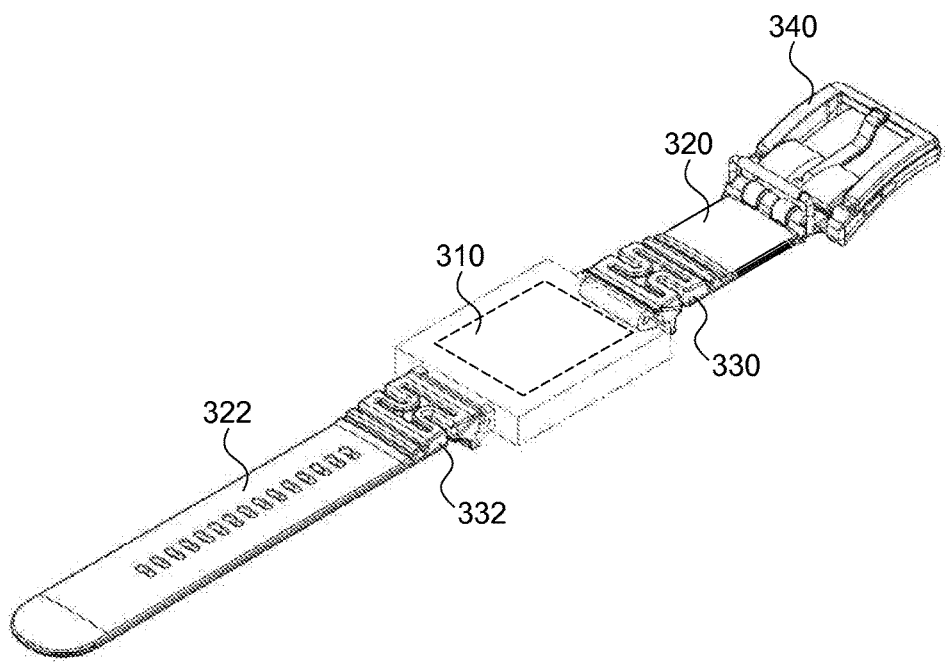

FIG. 1B is an appearance diagram showing a detailed configuration example of the biological information detection apparatus. The bands 320 and 322 are connected to the main body 300 through extension/contraction portions 330 and 332. The extension/contraction portions 330 and 332 are configured to be deformed along the first direction DR1, the second direction DR2, and the like of FIG. 1A. A connection 340 is connected to one end of the band 320. The connection 340 corresponds to a buckle in a timepiece, and a band hole into which a rod of the buckle is inserted is formed in the opposite band 322.

As shown in FIG. 2A, the connection 340 has a fixing member 342 which is fixed to the band 320, a slide member 344, or springs 350 and 352 as an elastic member. As shown in FIGS. 2B and 2C, the slide member 344 is slidably attached to the fixing member 342 along a slide direction DRS, and the springs 350 and 352 generate a tensile force during sliding. A load mechanism of this embodiment is realized by the springs 350 and 352, the extension/contraction portions 330 and 332, the bands 320 and 322, or the like.

An indicator 343 is provided in the fixing member 342, and a scale for indicating an appropriate slide range is attached to the indicator 343. Specifically, points P1 and P2 which indicate an appropriate slide range (pressing force range) are attached to the indicator 343. If the end portion on the band 320 side of the slide member 344 is located within the range of the points P1 and P2, it is ensured that the slide member is within an appropriate slide range (pressing force range), and an appropriate tensile force is applied. A user inserts the rod of the connection 340 corresponding to a buckle into the band hole of the band 322 so as to be within the appropriate slide range, and puts the biological information detection apparatus on his/her wrist. With this, it is ensured to some extent that the pressing force of the pulse wave sensor (a convex portion of a light transmitting member) to the subject becomes an assumed appropriate pressing force. The details of the structure of the biological information detection apparatus shown in FIGS. 1A to 2C are disclosed in JP-A-2012-90975.

In FIGS. 1A to 2C, although a case where the biological information detection apparatus is a timepiece type pulsimeter which is put on a wrist has been described as an example, this embodiment is not limited thereto. For example, the biological information detection apparatus of this embodiment may be a biological information detection apparatus which is put on a region (for example, a finger, an upper arm, a chest, or the like) other than a wrist to detect (measure) biological information. The biological information to be detected by the biological information detection apparatus is not limited to a pulse wave (pulse rate), and an apparatus which detects biological information (for example, a blood oxygen saturation level, body temperature, heartbeat, or the like) other than the pulse wave may be used.

Figure 3:
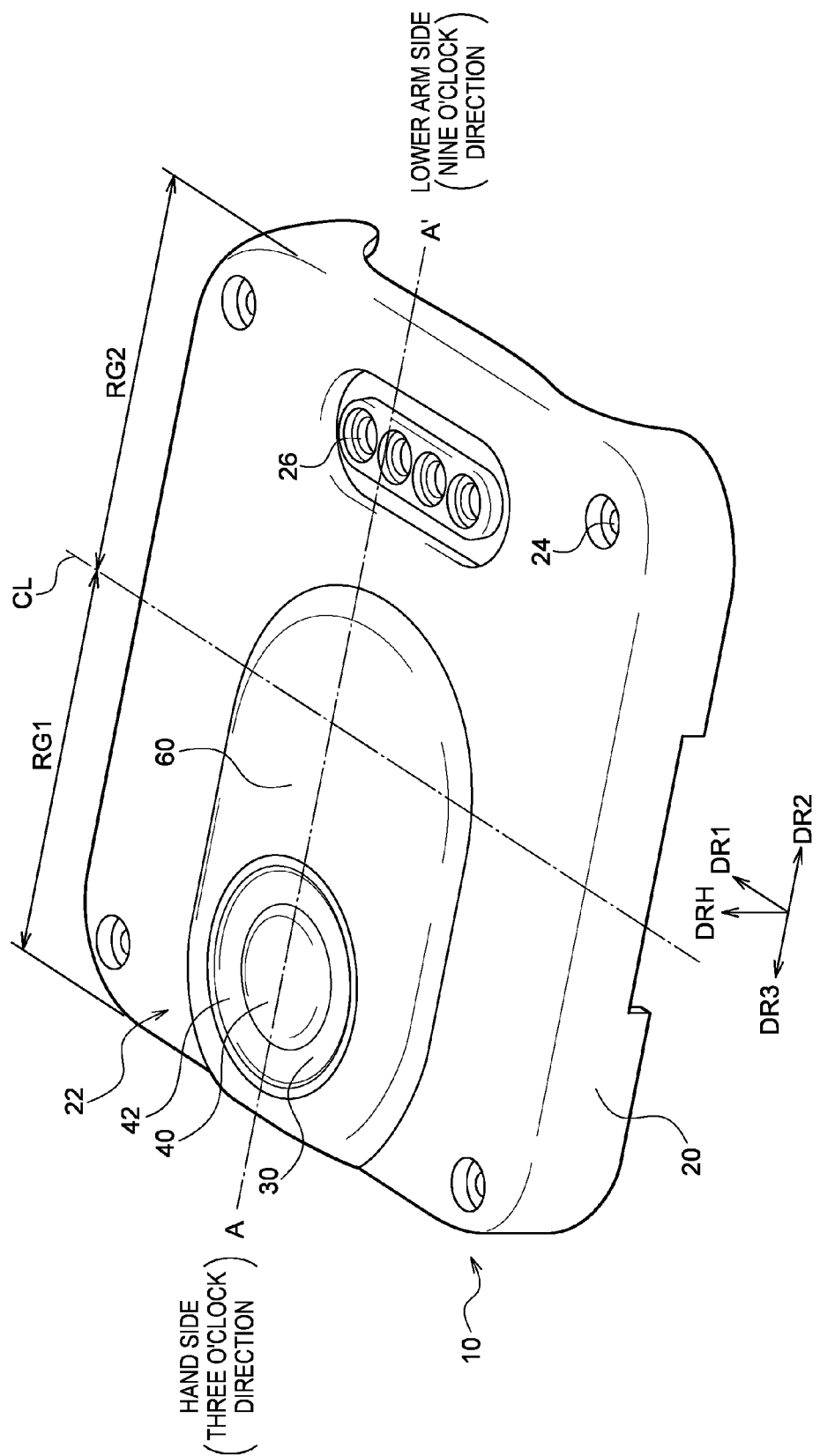
FIG. 3 is a perspective view of a rear lid of a main body of the biological information detection apparatus.
Figure 4:
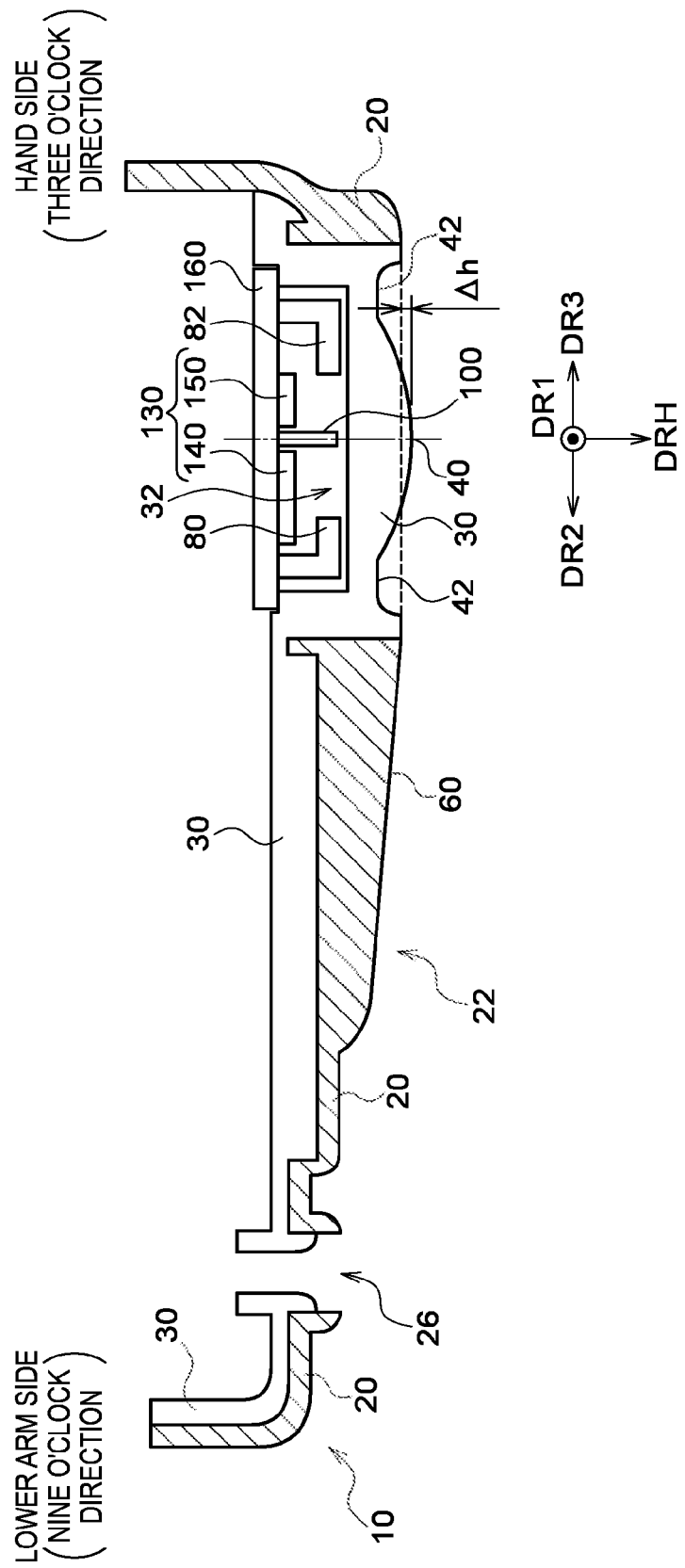
FIG. 4 is a sectional view of the rear lid.

FIG. 3 is a perspective view showing a configuration example of a rear lid 10 provided on the rear side of the main body 300 of the biological information detection apparatus, and FIG. 4 is a sectional view taken along the line IV-IV of FIG. 3. The rear lid 10 is constituted by a cover member 20 and a light transmitting member 30, and a housing surface 22 (rear surface) on the rear side of the main body 300 is constituted by the rear lid 10.

The light transmitting member 30 is provided on the housing surface 22 side in contact with the subject of the biological information detection apparatus, and transmits light from the subject. The light transmitting member 30 comes into contact with the subject when measuring the biological information of the subject. For example, a convex portion 40 of the light transmitting member 30 comes into contact with the subject. While it is preferable that the surface shape of the convex portion 40 is a curved shape (spherical shape), the invention is not limited thereto, and various shapes may be used. The light transmitting member 30 may be transparent to the wavelength of light from the subject, and a transparent material may be used, or a colored material may be used.

As shown in FIG. 4, the cover member 20 is formed so as to cover the light transmitting member 30. While the light transmitting member 30 has a light transmitting property, the cover member 20 is a non-light transmitting member having no light transmitting property. For example, the light transmitting member 30 is formed of transparent resin (plastic), and the cover member 20 is formed of resin of a predetermined color, such as black. The non-light transmitting property means the property of a material which does not transmit light of a wavelength to be detected by the biological information detection apparatus.

As shown in FIGS. 3 and 4, a part of the light transmitting member 30 is exposed from an opening of the cover member 20 toward the subject, and the convex portion 40 is formed in the exposed portion. Accordingly, when measuring the biological information, the convex portion 40 formed in the exposed portion comes into contact with the subject (for example, the skin of the wrist of the user). In FIGS. 3 and 4, a detection window of the biological information detection apparatus is constituted by the convex portion 40 formed in the exposed portion. In FIG. 4, the light transmitting member 30 is also provided in a portion other than the detection window, that is, a rear side portion of the cover member 20 (pressing force suppression unit 60). This embodiment is not limited thereto, and the light transmitting member 30 may be provided only in the portion of the detection window.

As shown in FIG. 4, a groove portion 42 for suppressing change in pressing force or the like is provided around the convex portion 40. When a surface of the light transmitting member 30 on the side on which the convex portion 40 is provided is defined as a first surface, the light transmitting member 30 has a concave portion 32 at a position corresponding to the convex portion 40 on a second surface on the rear side of the first surface. The rear lid 10 is provided with a screw hole 24 for fastening the rear lid 10, a terminal hole 26 for connecting a terminal for signal transfer or power supply, and the like.

As shown in FIG. 3, when the housing surface 22 (rear surface) of the biological information detection apparatus is divided into a first region RG1 and a second region RG2 by a central line CL along the first direction DR1, the convex portion 40 is provided in the first region RG1. For example, in the case of the biological information detection apparatus shown in FIG. 1A which is put on the wrist, the first region RG1 is a hand-side region (a three o'clock direction in a timepiece), and the second region RG2 is a lower arm-side region (a nine o'clock direction in a timepiece). In this way, the convex portion 40 of the light transmitting member 30 is provided in the first region RG1 close to the hand on the housing surface 22. With this, since the convex portion 40 is arranged at a location where there is small change in the diameter of the arm, it is possible to suppress change in pressing force or the like.

The convex portion 40 comes into contact with the subject when measuring the biological information of the subject and gives a pressing force. Specifically, when the user puts the biological information detection apparatus on his/her wrist to detect biological information, such as a pulse wave, the convex portion 40 comes into contact with the skin of the wrist of the user to give the pressing force. The pressing force is generated by a load of a load mechanism described in FIGS. 1A to 2C.

On the housing surface 22 of the biological information detection apparatus, a pressing force suppression unit 60 which suppresses the processing force to be given to the subject (the skin of the wrist) by the convex portion 40 is provided. In FIGS. 3 and 4, the pressing force suppression unit 60 is disposed in periphery of the convex portion 40 of the light transmitting member 30 on or above the housing surface 22. The surface of the cover member 20 functions as the pressing force suppression unit 60. That is, the surface of the cover member 20 is molded in a bank shape, whereby the pressing force suppression unit 60 is formed. As shown in FIG. 4, a pressing force suppression surface of the pressing force suppression unit 60 is inclined so as to be lowered in the second direction DR2 (a direction from the wrist toward the lower arm) from the position of the convex portion 40. That is, the height of a direction DRH orthogonal to the housing surface 22 is inclined so as to be lowered in the second direction DR2.

In FIGS. 3 and 4, although the detection unit 130 or the convex portion 40 (detection window) is provided in the first region RG1 on the hand side (three o'clock direction) of the housing surface 22 (rear surface), this embodiment is not limited thereto. For example, the detection unit 130 or the convex portion 40 (detection window) may be provided in a central region (a region through which a center line CL passes) or the like of the housing surface 22, and the pressing force suppression unit 60 may be provided in the periphery of the detection unit 130 or the convex portion 40 (detection window).

As shown in FIG. 4, the detection unit 130 is provided below the convex portion 40 of the light transmitting member 30. The upward direction is the direction DRH, and the downward direction is the direction opposite to the direction DRH. In other words, the downward direction is the direction from the rear surface (the surface on the side which comes into contact with the subject) of the main body 300 of the biological information detection apparatus toward the front surface (the surface on the side which does not come into contact with the subject). In this embodiment, the pulse wave sensor is a sensor unit which is constituted by the light transmitting member 30, the detection unit 130, or the like.

The detection unit 130 has a light receiving unit 140 and a light emitting unit 150. The light receiving unit 140 and the light emitting unit 150 are mounted on a substrate 160. The light receiving unit 140 receives light (reflected light, transmitted light, or the like) from the subject. The light emitting unit 150 emits light to the subject. For example, if the light emitting unit 150 emits light to the subject, and light is reflected by the subject (blood vessel), the light receiving unit 140 receives and detects the reflected light. The light receiving unit 140 can be realized by, for example, a light receiving element, such as a photodiode. The light emitting unit 150 can be realized by a light emitting element, such as an LED. For example, the light receiving unit 140 can be realized by a PN junction diode element formed on a semiconductor substrate. In this case, an angle limiting filter for narrowing a light receiving angle or a wavelength limiting filter for limiting the wavelength of light entering the light receiving element may be formed on the diode element.

In the case of a pulsimeter as an example, light from the light emitting unit 150 travels inside the subject, and is diffused or scattered by an epidermis, a corium, a subcutaneous tissue, and the like. Thereafter, light reaches the blood vessel (a region to be detected) and is reflected. At this time, a part of light is absorbed by the blood vessel. Since the absorption rate of light in the blood vessel changes due to the effect of a pulse, and the amount of reflected light also changes, the light receiving unit 140 receives the reflected light to detect change in the amount of light, thereby detecting a pulse rate or the like as biological information.

In FIG. 4, although both the light receiving unit 140 and the light emitting unit 150 are provided as the detection unit 130, for example, only the light receiving unit 140 may be provided. In this case, for example, the light receiving unit 140 receives transmitted light from the subject. For example, when light from the light emitting unit 150 provided on the rear side of the subject transmits through the subject, the light receiving unit 140 receives and detects the transmitted light.

In this embodiment, as shown in FIG. 4, diaphragm units 80 and 82 are provided. When the light receiving unit 140 is provided as the detection unit 130, the diaphragm units 80 and 82 narrow light from the subject in an optical path between the subject and the detection unit 130. When the light emitting unit 150 is provided as the detection unit 130, the diaphragm units 80 and 82 narrow light from the light emitting unit 150 in an optical path between the subject and the detection unit 130. In FIG. 4, the diaphragm units 80 and 82 are provided between the light transmitting member 30 and the detection unit 130. However, the diaphragm units 80 and 82 may be provided between the light transmitting member 30 and the subject or inside the light transmitting member 30. For example, the diaphragm units 80 and 82 are arranged near the light transmitting member 30.

In FIG. 4, a light shielding unit 100 is provided between the light receiving unit 140 and the light emitting unit 150. When both the light receiving unit 140 and the light emitting unit 150 are provided as the detection unit 130, for example, the light shielding unit 100 shields light from the light emitting unit 150 to suppress the direct entrance to the light receiving unit 140.

2. Diaphragm Unit, Light Shielding Unit

In the biological information detection apparatus of this embodiment, in the light transmitting member 30, a surface which comes into contact with skin as the subject becomes a contact surface having a finite area. In this embodiment, for example, a relatively soft subject, such as skin, comes into contact with the contact surface having a finite area of the light transmitting member 30 formed of a hard material, such as resin or glass. Then, from the viewpoint of theory of elasticity, a region which does not come into contact with skin or a region where a contact pressure is weak occurs near the marginal portion (peripheral portion) of the light transmitting member 30. Even when an external force is applied to the instrument of the biological information detection apparatus, and momentum is generated in the instrument, a region near the marginal portion of the contact surface is most likely to be steady.

In light passing among the light emitting unit 150, skin, the light receiving unit 140 through this region, light intensity is likely to be optically generated due to change in dynamic contact state. If light enters the light receiving unit 140, light becomes noise having no correlation with a pulse component.

Even in a static contact state, signal quality may be degraded. If there is no proper contact with skin, external light which does not arise from the light emitting unit 150 enters the light receiving unit 140. When the contact pressure is excessive, a subcutaneous blood vessel is crushed, whereby a pulsation component is less brought into light which passes through this region.

As such noise is greatly superimposed, signal quality of the pulse wave detection signal is degraded, and in various kinds of biological measurements, such as pulse measurement, reliability of measured data is degraded.

Figure 5B:
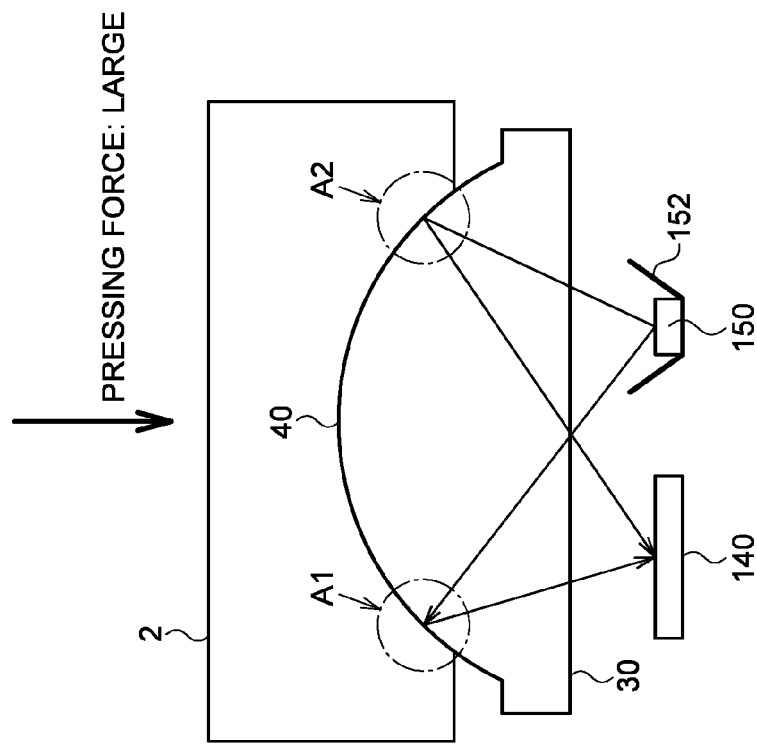
FIGS. 5A and 5B are explanatory views of a problem when a pressing force of a light transmitting member to a subject changes.
Figure 5A:
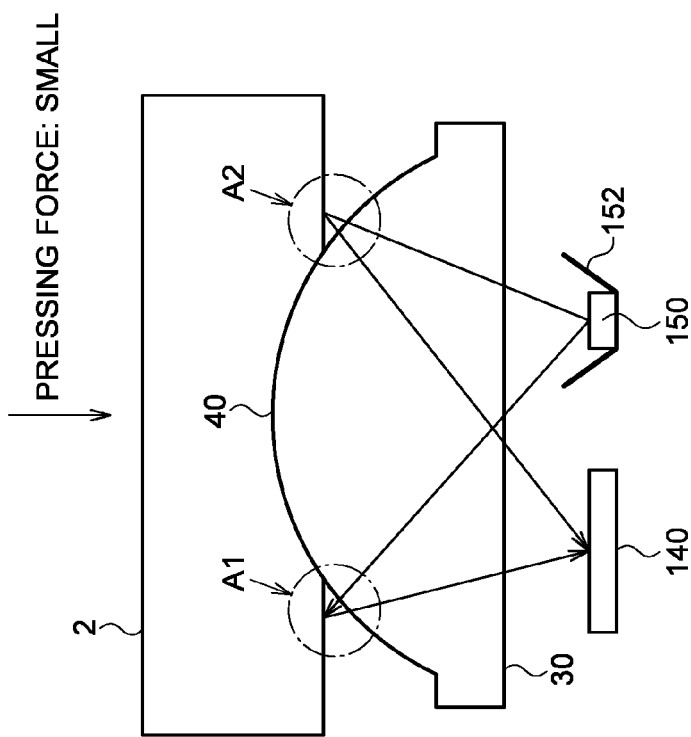

For example, FIG. 5A shows a case where a pressing force given to skin 2 as the subject by the convex portion 40 (contact surface) of the light transmitting member 30 is small, and FIG. 5B shows a case where the pressing force is large. Focusing on the locations indicated by A1 and A2 shown in FIGS. 5A and 5B, change in pressing force causes change in the contact state between the skin 2 and the convex portion 40. For example, in FIG. 5A, while the skin 2 and the convex portion 40 are in a non-contact state or a weak contact state at the locations of A1 and A2, in FIG. 5B, the skin 2 and the convex portion 40 are in the contact state. Accordingly, intensity or the like of light which is emitted from the light emitting unit 150 and returns to the light receiving unit 140 changes between FIGS. 5A and 5B, and reliability of measured data is degraded. FIGS. 5A and 5B may be interpreted as an enlarged view of the periphery of the concave portion 32 in the sectional view of the biological information detection apparatus taken along the line A-A' shown in FIG. 3, or may be interpreted as a projection diagram or an arrangement diagram in which the components in the periphery of the concave portion 32 from the vertical direction with respect to the direction DRH. Hereinafter, although this embodiment will be described using similar diagrams of FIGS. 5A and 5B, it is assumed that all drawings can be interpreted in the same manner.

Figure 6A:
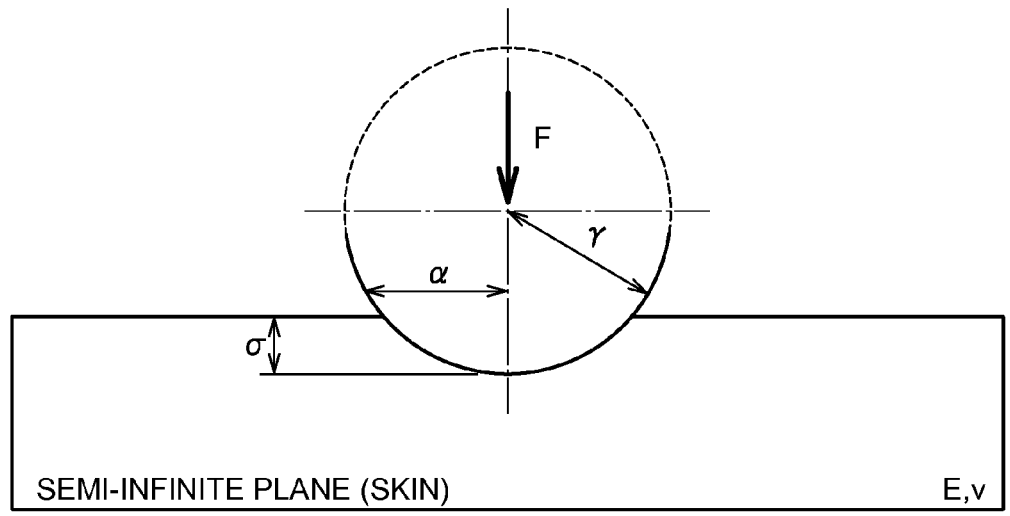
FIGS. 6A and 6B are explanatory views of Hertz elastic contact theory.
Figure 6B:
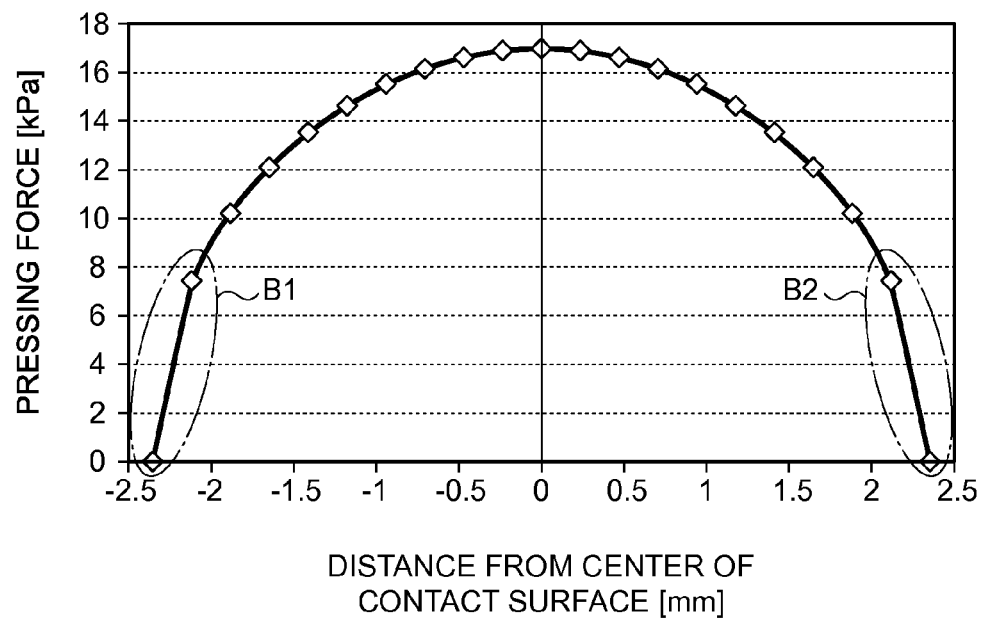

For example, FIGS. 6A and 6B are diagrams illustrating Hertz elastic contact theory. E is a Young's modulus of skin, v is a Poisson's ratio of skin, F is a maximum value of a force to be applied, r is a spherical radius, $\alpha$ is a radius of a contact round surface, and $\sigma$ is a displacement. If predetermined values are substituted in these parameters, and the pressing force with respect to the distance from the center of the contact surface is calculated on the basis of Hertz elastic contact theory, for example, a result shown in FIG. 6B is obtained. As shown in FIG. 6B, if the distance from the center of the contact surface increases, the pressing force decreases, and for example, in the portions indicated by B1 and B2, the pressing force abruptly decreases. Accordingly, at the locations indicated by A1 and A2 of FIGS. 5A and 5B, slight change in load causes abrupt change in the pressing force on the contact surface, and reliability of measured data is significantly degraded.

For example, in FIGS. 5A and 5B, the contact surface of the light transmitting member 30 which comes into contact with skin of a human has a curved convex shape (convex portion). With this, since the degree of adhesion of the light transmitting member 30 to the surface of skin is improved, it is possible to prevent intrusion of noise light, such as the amount of reflected light from the surface of skin or ambient light.

However, as will be apparent from FIGS. 6A and 6B, in the marginal portion (peripheral portion) of the convex shape, the contact pressure with skin relatively decreases with respect to the center portion.

In this case, if optimization is made with the contact pressure of the center portion, the contact pressure of the marginal portion is less than an optimum range. If optimization is made with the contact pressure of the marginal portion, the contact pressure of the center portion is excessive with respect to the optimum range.

When the contact pressure is less than the optimum range, in a case where the pulse wave sensor comes into contact with skin or is detached from skin due to shaking of the apparatus, or even if the pulse wave sensor is in contact with skin, the pulse wave sensor does not crush the vein completely, whereby body motion noise is superimposed on the pulse wave detection signal. If the noise component is reduced, it becomes possible to obtain a pulse wave detection signal having a higher M/N ratio (S/N ratio). Here, M represents a signal level of the pulse wave detection signal, and N represents a noise level.

In order to solve the above-described problem, as shown in FIGS. 4, 7A, and 7B, the biological information detection apparatus of this embodiment has the detection unit 130 which has the light receiving unit 140 receiving light from the subject (skin or the like), the light transmitting member 30, and the diaphragm units 80 and 82 (aperture). The light transmitting member 30 is provided on the housing surface 22 side which comes into contact with the subject of the biological information detection apparatus, transmits light from the subject, and comes into contact with the subject when measuring the biological information of the subject. The diaphragm units 80 and 82 narrow light from the subject in the optical path between the subject and the detection unit 130. In FIG. 4 and the like, the detection unit 130 has the light emitting unit 150 which emits light to the subject, and the light transmitting member 30 transmits light from the light emitting unit 150. The diaphragm units 80 and 82 narrow light from the light emitting unit 150 in the optical path between the subject and the detection unit 130. A reflector 152 reflects light emitted from the light emitting unit 150 to increase light use efficiency.

In this way, in this embodiment, the diaphragm units 80 and 82 are provided such that light (stray light) at the locations or the like indicated by A1 and A2 of FIGS. 7A and 7B is not detected, and narrow light. For example, light which passes through the center portion (for example, the vertex of the convex portion) of the light transmitting region of the light transmitting member 30 with an optimum pressing force is transmitted as much as possible without being shielded, and light near the marginal portion of the light transmitting region (for example, the convex portion) of the light transmitting member 30 is shielded. For example, in FIGS. 7A and 7B, the diaphragm unit 80 is provided such that light at the location indicated by A1 in the marginal portion does not enter the light receiving unit 140. The diaphragm unit 82 is provided such that light from the light emitting unit 150 is not emitted to the location indicated by A2. That is, in this embodiment, light at a location where change in pressing force (load) causes change in the contact state is narrowed. With this configuration, as shown in FIGS. 7A and 7B, even when the contact state changes at the locations indicated by A1 and A2, the states of light at the locations indicated by A1 and A2 do not affect a light receiving result. Accordingly, it is possible to improve reliability of measured data or the like.

In FIGS. 4, 7A, 7B, and the like, the light shielding unit 100 (light shielding wall) is provided between the light receiving unit 140 the light emitting unit 150. The light shielding unit 100 is, for example, a light shielding wall which is formed to extend in the direction DRH orthogonal to the housing surface 22 (see FIGS. 3 and 4). Specifically, for example, the light shielding unit 100 which has a wall surface along a direction intersecting (orthogonal to) a line segment connecting the center position of the light receiving unit 140 and the center position of the light emitting unit 150 is provided. The light shielding unit 100 is provided such that the entrance of direct light from the light emitting unit 150 to the light receiving unit 140 is inhibited, thereby further improving reliability of measured data or the like.

That is, as the distance between the light receiving unit 140 and the light emitting unit 150 decreases, optical efficiency or performance is improved. For example, optical efficiency or performance is deteriorated in inverse proportion to the square of the distance. Accordingly, it is preferable to decrease the distance between the light receiving unit 140 and the light emitting unit 150 as small as possible.

However, if the distance between the light receiving unit 140 and the light emitting unit 150 decreases, there is an increasing possibility that direct light from the light emitting unit 150 enters the light receiving unit 140 and performance is deteriorated.

Accordingly, the light shielding unit 100 is provided between the light receiving unit 140 and the light emitting unit 150 to inhibit direct light from the light emitting unit 150 from entering the light receiving unit 140. That is, in this embodiment, as described above, in order to eliminate optical adverse effects from a path in which the contact state of the subject and the contact surface becomes unstable, the diaphragm units 80 and 82 are provided. The adverse effects by direct light of the light emitting unit 150 is eliminated by the light shielding unit 100. With this configuration, it becomes possible to ensure optical stability of a photoelectric pulse wave sensor by the diaphragm units 80 and 82 which eliminate noise due to change in the contact state of the subject and the contact surface, and the light shielding unit 100 which eliminates direct light of the light emitting unit 150. The light shielding unit 100 may not be provided.

Figure 8A:
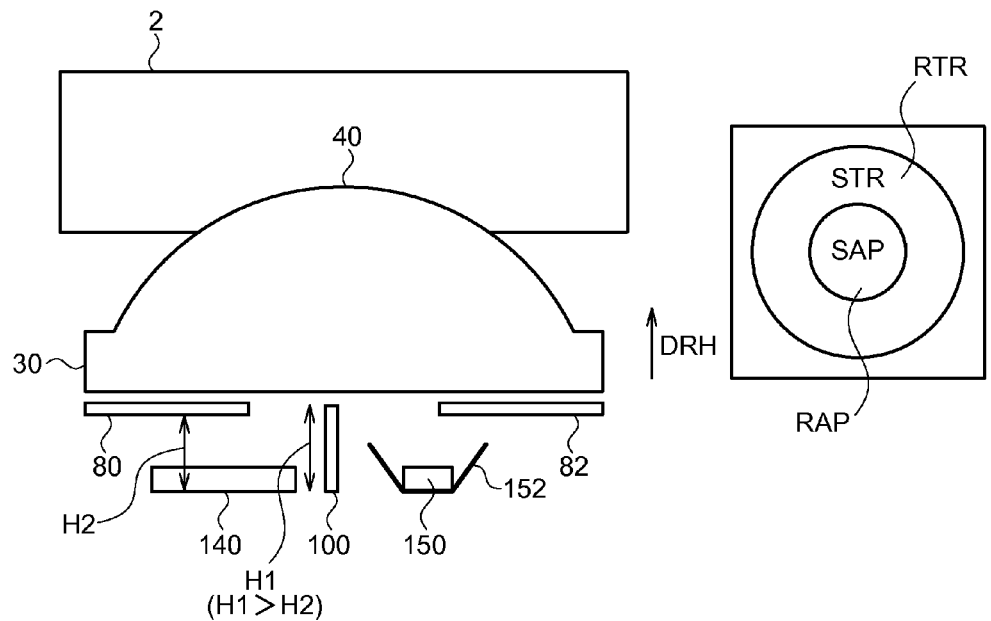
FIGS. 8A and 8B are diagrams showing an arrangement configuration example of a diaphragm unit and a light shielding unit.
Figure 8B:
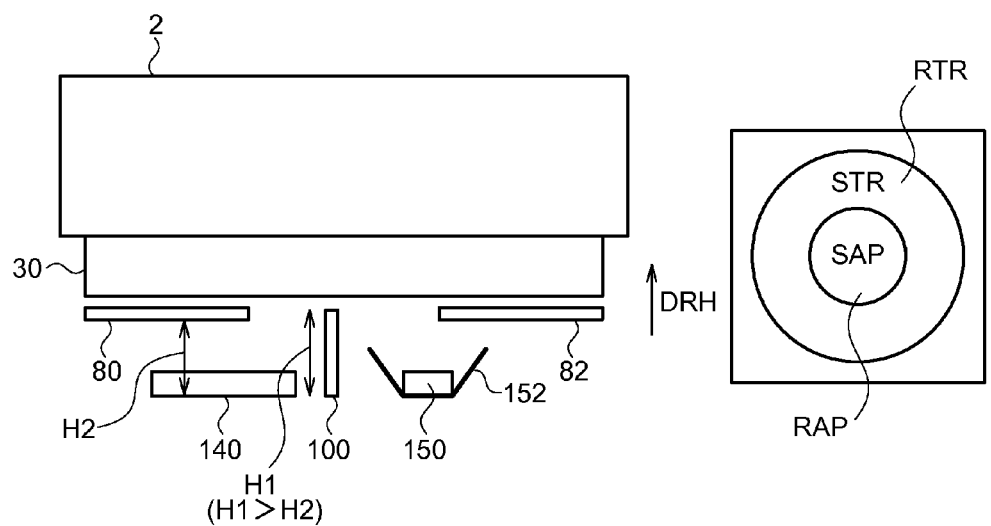

As shown in FIG. 8A, although a case where the light transmitting member 30 has the convex portion 40 has been described, the biological information detection apparatus of this embodiment is not limited thereto. For example, as shown in FIG. 8B, even when the light transmitting member 30 has no curved convex portion 40 or the like, the diaphragm units 80 and 82 or the light shielding unit 100 is provided, thereby suppressing degradation of reliability of measured data or the like due to stray light. For example, the light transmitting member 30 has a three-dimensional shape in which a non-planar portion comes into contact with an object, and the diaphragm units 80 and 82 are provided so as to shield light of a relatively low portion in the three-dimensional shape.

In FIGS. 8A and 8B, RTR represents a light transmitting region (a region which transmits light) of the light transmitting member 30, and RAP represents a diaphragm region (a region which narrows light) of each of the diaphragm units 80 and 82. STR represents the area of the light transmitting region RTR, and SAP represents the area of the diaphragm region RAP. For example, in FIG. 3, in the light transmitting member 30, a region which is not covered with the cover member 20 and is exposed toward the subject becomes the light transmitting region RTR. The diaphragm region RAP is the region of the opening of each of the diaphragm units 80 and 82. The diaphragm region RAP of each of the diaphragm units 80 and 82 becomes a region which is surrounded by the light transmitting region RTR, for example, in plan view.

Specifically, as shown in FIGS. 8A and 8B, the area SAP of the diaphragm region RAP (opening region) of each of the diaphragm units 80 and 82 is smaller than the area STR of the light transmitting region RTR of the light transmitting member 30. That is, the diaphragm units 80 and 82 shield light which passes through the marginal region (circumferential region) of the light transmitting member 30, and the area SAP is smaller than the area STR by the area of at least the marginal region.

In FIGS. 8A and 8B, the shape of the diaphragm region RAP of each of the diaphragm units 80 and 82 is a similar shape (including a substantially similar shape) to the shape of the light transmitting region RTR of the light transmitting member 30. As in FIG. 8A, when the light transmitting member 30 has the convex portion 40, the shape of the light transmitting region RTR is a similar shape (a substantially similar shape) to, for example, a plane projection shape of the convex portion 40. For example, in FIGS. 8A and 8B, all the shapes of the light transmitting region RTR and the diaphragm region RAP are circular shapes and are similar shapes. For example, when the light transmitting region RTR has a quadrangular shape, the shape of the diaphragm region RAP may be a similar shape, that is, a quadrangular shape. However, the similar shape is not necessarily a completely similar shape, and may be a substantially similar shape (a similar shape as the type of a figure). The shape of the light transmitting region RTR and the shape of the diaphragm region RAP may not be similar shapes.

In FIGS. 8A and 8B, if the height of the light shielding unit 100 in the direction DRH orthogonal to the housing surface 22 of FIGS. 3 and 4 is referred to as H1, and the height of the lower surface which is the surface on the detection unit side of each of the diaphragm units 80 and 82 is referred to as H2, the relationship H1>H2 is established. With this configuration, it is possible to suppress a situation in which light from the light emitting unit 150 is reflected by the diaphragm units 80 and 82 or the like and enters the light receiving unit 140.

Figure 9A:
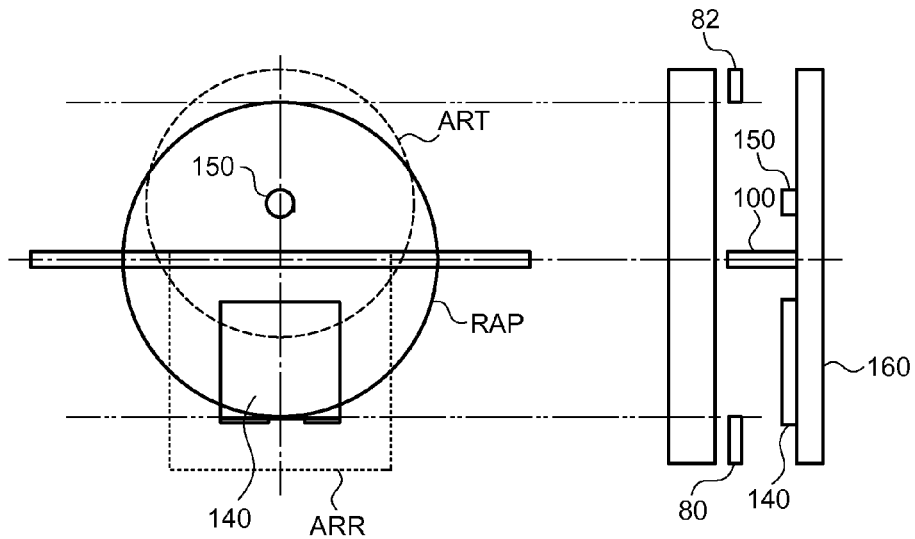
FIGS. 9A to 9C are explanatory views of a method of setting a hole diameter of a diaphragm region.
Figure 9B:
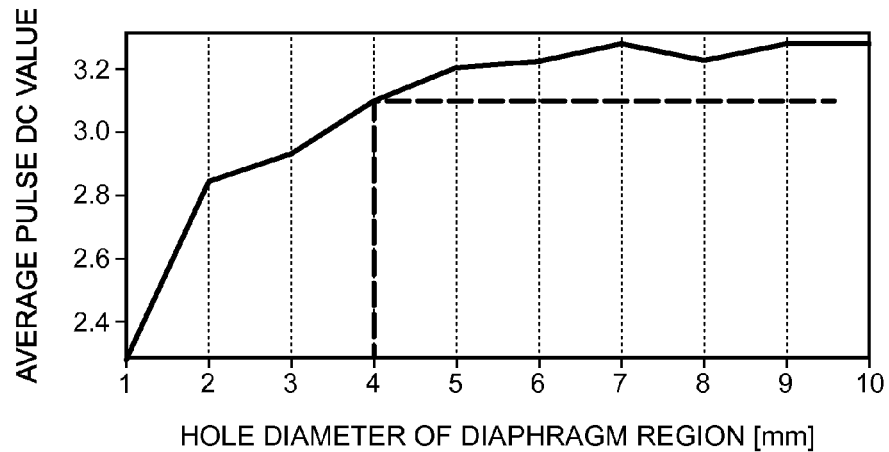
Figure 9C:
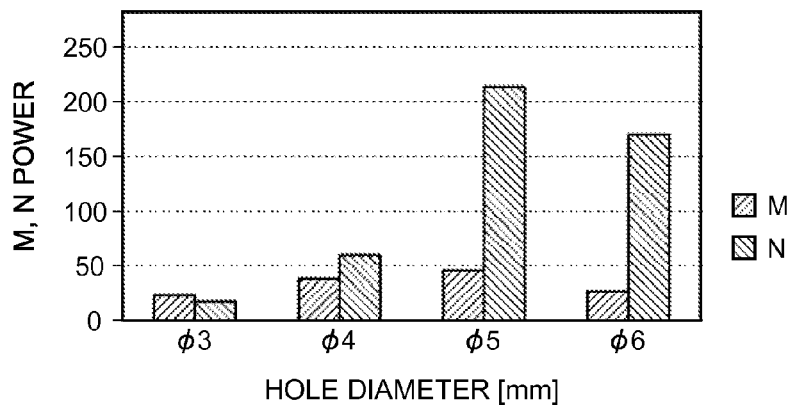

FIGS. 9A to 9C are explanatory views of a method of setting a hole diameter of the diaphragm region RAP. In FIG. 9A, ARR represents a light receiving area of the light receiving unit 140, and ART represents a light irradiating area of the light emitting unit 150. The light receiving area ARR and the light irradiating area ART are the areas which are set by a half-value width of light intensity. The diaphragm region RAP can be determined by the light receiving area ARR and the light irradiating area ART. For example, the diaphragm region RAP is the region which includes at least the area on the light shielding unit 100 side (on the center side) out of the light receiving area ARR and the light irradiating area ART.

FIG. 9B is a diagram showing the relationship between a hole diameter (transmission hole diameter) of the diaphragm region RAP and an average pulse wave DC value. As shown in FIG. 9B, since the amount of light to be transmitted increases as the hole diameter of the diaphragm region RAP increases, the average pulse wave DC value increases. However, an increase in the average pulse wave DC value with respect to an increase in the hole diameter of the diaphragm region RAP is saturated. For example, in FIG. 9B, saturation occurs at a point at which the hole diameter of the diaphragm region RAP is about 4 mm.

FIG. 9C is a diagram showing the relationship between a hole diameter (aperture diameter) of the diaphragm region RAP and M and N power. Here, M represents a signal level of a pulse wave signal, and N represents a noise level. As shown in FIG. 9C, if the hole diameter is greater than 5 mm, the noise level increases abruptly. As described referring to FIGS. 5A and 5B, this is because, if the hole diameter increases, stray light in the marginal region of the light transmitting member 30 enters the light receiving unit 140 and is detected as noise.

In this way, if the hole diameter of the diaphragm region RAP is excessively small, the amount of received light decreases, and the level of the pulse wave detection signal is degraded. Meanwhile, if the hole diameter of the diaphragm region RAP is excessively large, the noise component increases due to stray light or the like in the marginal region of the light transmitting member 30. Accordingly, it is preferable that the hole diameter of the diaphragm region RAP is set to a value for minimizing the effect due to change (that is, noise) in the contact state with the subject (skin, hide) in a range in which the level of the pulse wave detection signal can be sufficiently ensured. For example, in FIGS. 9A to 9C, the hole diameter is set to about 4 mm ($\phi 4$).

FIGS. 10A to 11B are explanatory views of a method of arranging and setting a diaphragm unit.

Figure 10A:
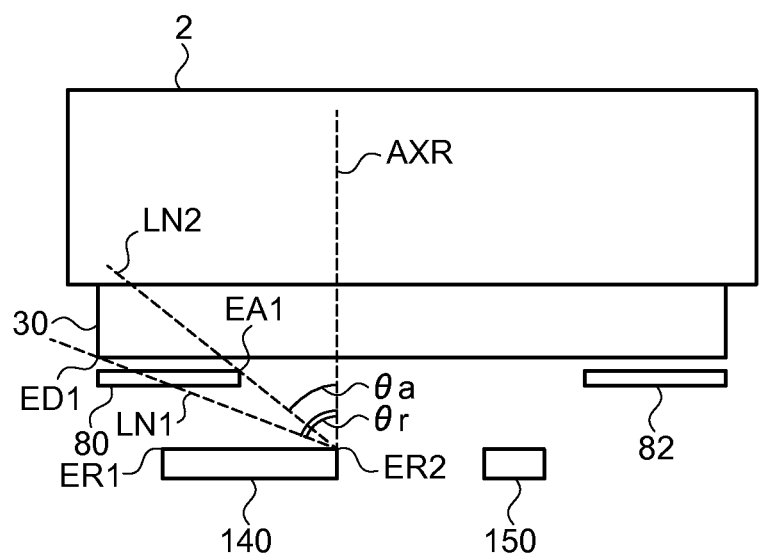
FIGS. 10A and 10B are explanatory views of a method of arranging and setting the diaphragm unit.

For example, in FIG. 10A, a line which connects a first end portion ED1 (an end portion on the light receiving unit side) of the light transmitting region of the light transmitting member 30 and a second end portion ER2 (right end portion) of the light receiving unit 140 is referred to as LN1. The second end portion ER2 is an end portion away from the first end portion ED1 of the light transmitting region out of two end portions ER1 and ER2 of the light receiving unit 140. A line which connects the second end portion ER2 of the light receiving unit 140 and the end portion EA1 on the opening side of the diaphragm unit 80 is referred to as LN2. The angle between the line LN1 and an optical axis AXR (an axis perpendicular to a light receiving surface) of the light receiving unit 140 is referred to as θr, and the angle between the line LN2 and the optical axis AXR is referred to as θa.

In this case, in FIG. 10A, θa<θr. That is, the diaphragm unit 80 on the light receiving unit 140 side is arranged and set such that θa<θr.

In this way, if the relationship θa<θr is established, as will be apparent from FIG. 10A, light from the first end portion ED1 of the light transmitting region of the light transmitting member 30 is shielded by the diaphragm unit 80, such that light does not enter the light receiving unit 140.

For example, since the light receiving unit 140 detects the amount of received light on the entire light receiving surface, even if light enters the second end portion ER2, light is detected as the overall amount of received light. Accordingly, if the state of light entering the second end portion ER2 of the light receiving unit 140 from the first end portion ED1 of the light transmitting member 30 changes due to change in the contact state or the like, this change is superimposed as noise, and there is a situation in which reliability of measured data or the like is degraded.

In this regard, as shown in FIG. 10A, if the relationship θa<θr is established, since light from the first end portion ED1 of the light transmitting region of the light transmitting member 30 is shielded by the diaphragm unit 80, it is possible to effectively inhibit the situation as described above.

Figure 10B:
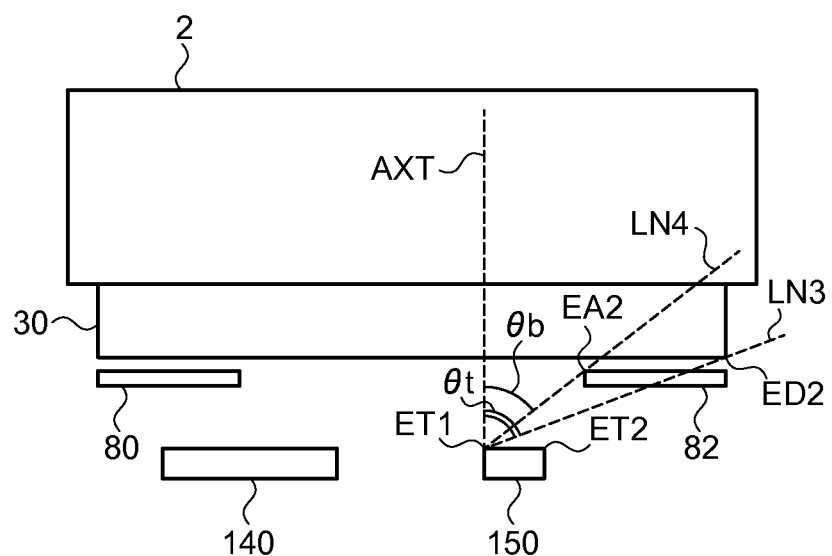

In FIG. 10B, a line which connects a second end portion ED2 (an end portion on the light emitting unit side) of the light transmitting region of the light transmitting member 30 and a first end portion ET1 (left end portion) of the light emitting unit 150 is referred to as LN3. The first end portion ET1 is an end portion away from the second end portion ED2 of the light transmitting region out of two end portions ET1 and ET2 of the light emitting unit 150. A line which connects the first end portion ET1 of the light emitting unit 150 and the end portion EA2 on the opening side of the diaphragm unit 82 is referred to as LN4. The angle between the line LN3 and an optical axis AXT (an axis perpendicular to a light emitting surface) of the light emitting unit 150 is referred to as θt, and the angle between the line LN4 and the optical axis AXT is referred to as θb.

In this case, in FIG. 10B, θb<θt. That is, the diaphragm unit 82 on the light emitting unit 150 side is arranged and set such that θb<θt.

In this way, if the relationship θb<θt is established, as will be apparent from FIG. 10B, light from the light emitting unit 150 toward the second end portion ED2 of the light transmitting region of the light transmitting member 30 is shielded by the diaphragm unit 82. Accordingly, it is possible to effectively inhibit a situation in which stray light in the second end portion ED2 is received, or the like.

Figure 11A:
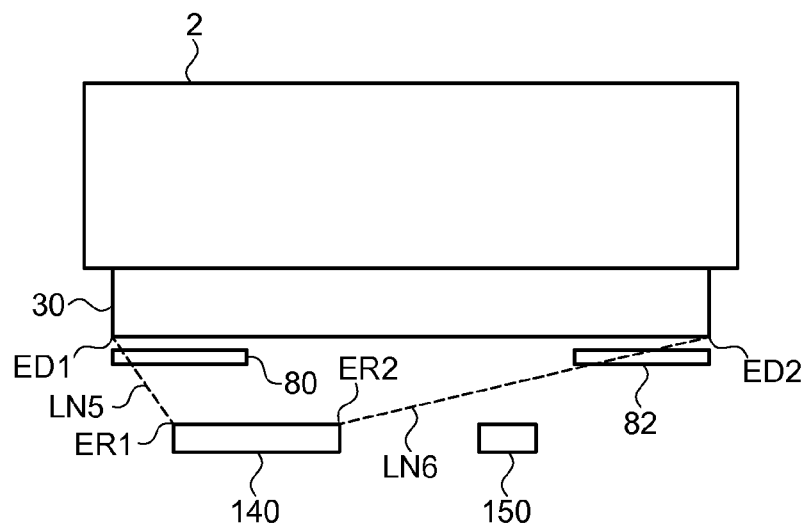
FIGS. 11A and 11B are explanatory views of the method of arranging and setting the diaphragm unit.
Figure 11B:
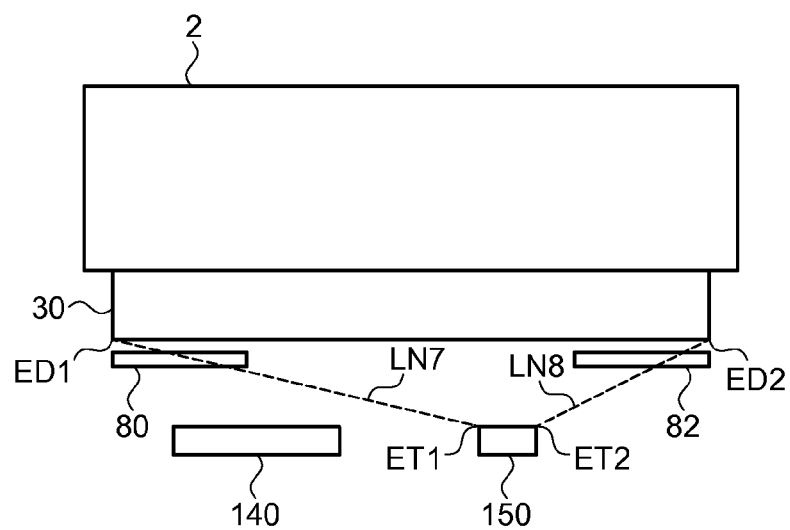

The diaphragm units 80 and 82 may be arranged and set by the method shown in FIGS. 11A and 11B.

For example, in FIG. 11A, a line which connects the first end portion ED1 (the end portion on the light receiving unit side) of the light transmitting region of the light transmitting member 30 and the first end portion ER1 (left end portion) of the light receiving unit 140 is referred to as LN5. The first end portion ER1 is an end portion close to the first end portion ED1 of the light transmitting region out of the two end portions ER1 and ER2 of the light receiving unit 140. A line which connects the second end portion ED2 (the end portion on the light emitting unit side) of the light transmitting region of the light transmitting member 30 and the second end portion ER2 (right end portion) of the light receiving unit 140 is referred to as LN6. The second end portion ER2 is an end portion close to the second end portion ED2 of the light transmitting region out of the two end portions ER1 and ER2 of the light receiving unit 140.

In this case, in FIG. 11A, the diaphragm units 80 and 82 are arranged and set such that the diaphragm units 80 and 82 are located on at least the lines LN5 and LN6. That is, the diaphragm units 80 and 82 are located on the optical path of the lines LN5 and LN6.

With this configuration, it can be ensured that stray light from the first and second end portions ED1 and ED2 of the light transmitting region of the light transmitting member 30 is shielded by the diaphragm units 80 and 82. Accordingly, it is possible to effectively suppress a situation in which reliability of measured data or the like is degraded due to stray light in the first and second end portions ED1 and ED2.

In FIG. 11B, a line which connects the first end portion ED1 of the light transmitting region of the light transmitting member 30 and the first end portion ET1 (left end portion) of the light emitting unit 150 is referred to as LN7. The first end portion ET1 is an end portion close to the first end portion ED1 of the light transmitting region out of the two end portions ET1 and ET2 of the light emitting unit 150. A line which connects the second end portion ED2 of the light transmitting region of the light transmitting member 30 and the second end portion ET2 (right end portion) of the light emitting unit 150 is referred to as LN8. The second end portion ET2 is an end portion close to the second end portion ED2 of the light transmitting region out of the two end portions ET1 and ET2 of the light emitting unit 150.

In this case, in FIG. 11B, the diaphragm units 80 and 82 are arranged and set such that the diaphragm units 80 and 82 are located on at least the lines LN7 and LN8. That is, the diaphragm units 80 and 82 are located on the optical path of the lines LN7 and LN8.

With this configuration, it can be ensured such that light from the light emitting unit 150 toward the first and second end portions ED1 and ED2 of the light transmitting region of the light transmitting member 30 is shielded by the diaphragm units 80 and 82. Accordingly, it is possible to effectively suppress a situation in which light from the light emitting unit 150 becomes stray light in the first and second end portions ED1 and ED2, and reliability of measured data or the like is degraded due to stray light.

In FIGS. 4, 7A, 7B, and the like, the diaphragm units 80 and 82 are provided between the light transmitting member 30 and the detection unit 130 (light receiving unit 140, light emitting unit 150). For example, the diaphragm units 80 and 82 are arranged and set at the positions away from the light transmitting member 30 or the detection unit 130. In this way, if the diaphragm units 80 and 82 are arranged between the light transmitting member 30 and the detection unit 130, stray light is effectively shielded by the diaphragm units 80 and 82 on the optical path between the subject and the detection unit 130, thereby effectively suppressing a situation in which noise due to stray light is superimposed on measured data. However, the method of arranging and setting the diaphragm units 80 and 82 is not limited thereto, various modifications may be made, and the diaphragm units 80 and 82 may be provided between the light transmitting member 30 and the subject or inside the light transmitting member 30.

Figure 12A:
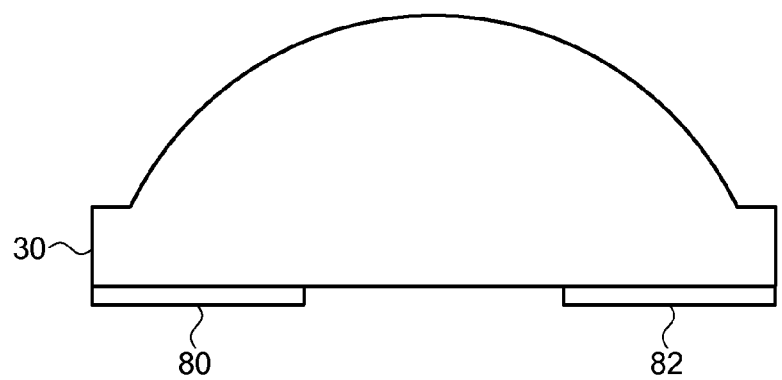
FIGS. 12A to 12C are diagrams showing various examples of an arrangement position of the diaphragm unit.
Figure 12B:
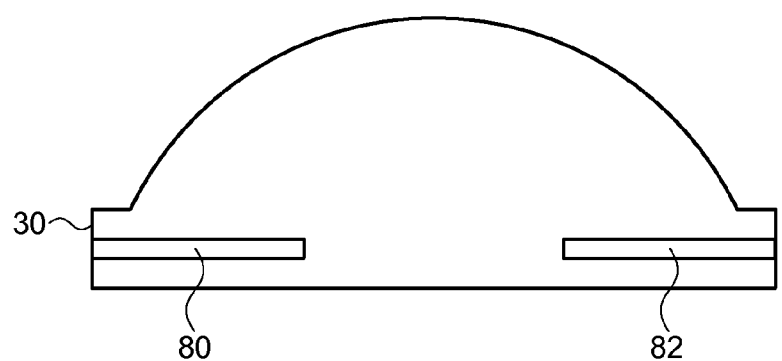
Figure 12C:
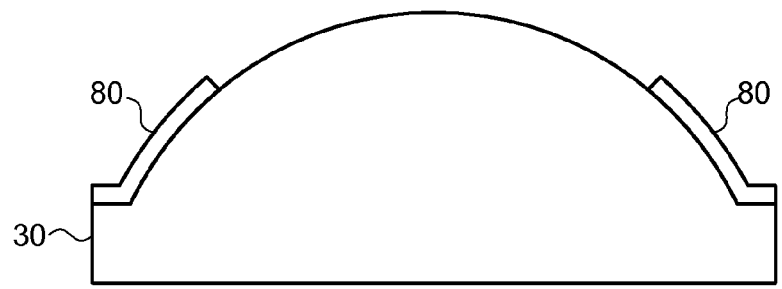

For example, in FIG. 12A, while the diaphragm units 80 and 82 are provided between the light transmitting member 30 and the detection unit 130, the diaphragm units 80 and 82 are arranged and set so as to be in close contact with the light transmitting member 30. In FIG. 12B, the diaphragm units 80 and 82 are arranged and set inside the light transmitting member 30 (in the material). In FIG. 12C, the diaphragm units 80 and 82 are arranged and set between the subject and the light transmitting member 30. In this way, as the method of arranging and forming the diaphragm units 80 and 82, various forms may be assumed.

A method of manufacturing the diaphragm units 80 and 82 is not limited to a method of forming diaphragm units 80 and 82 separately from the light transmitting member 30 or the like as in FIGS. 4, 7A, 7B, and the like, and various methods may be used. For example, as in FIGS. 12A and 12C, when forming the diaphragm units 80 and 82 so as to be in close contact with the light transmitting member 30, the diaphragm units 80 and 82 may be formed by a method, such as painting, vapor deposition, or printing. Alternatively, as in FIG. 12B, when forming the diaphragm units 80 and 82 in the light transmitting member 30, for example, the diaphragm units 80 and 82 may be formed by a method, such as insert molding.

The shape of the diaphragm region (aperture) of each of the diaphragm units 80 and 82 may be a similar shape (substantially similar shape, pseudo similar shape) to the light transmitting region of the light transmitting member 30, or may be a similar shape (substantially similar shape, pseudo similar shape) to the structure of the light receiving unit 140 or the convex portion 40. Alternatively, a similar shape (substantially similar shape, pseudo similar shape) to the light receiving range of the light receiving unit 140 or the light emitting range of the light emitting unit 150 may be used.

According to the biological information detection apparatus of this embodiment described above, emitted light which passes through a region where a contact pressure of the pulse wave sensor and skin is weak or a region where the contact state of the pulse wave sensor and skin is likely to change, or diffused light from skin is shielded, making it possible to reduce the noise component which is superimposed on the pulse wave detection signal and to improve signal quality.

3. Integral Forming of Diaphragm Unit and Light Shielding Unit

Figure 13:
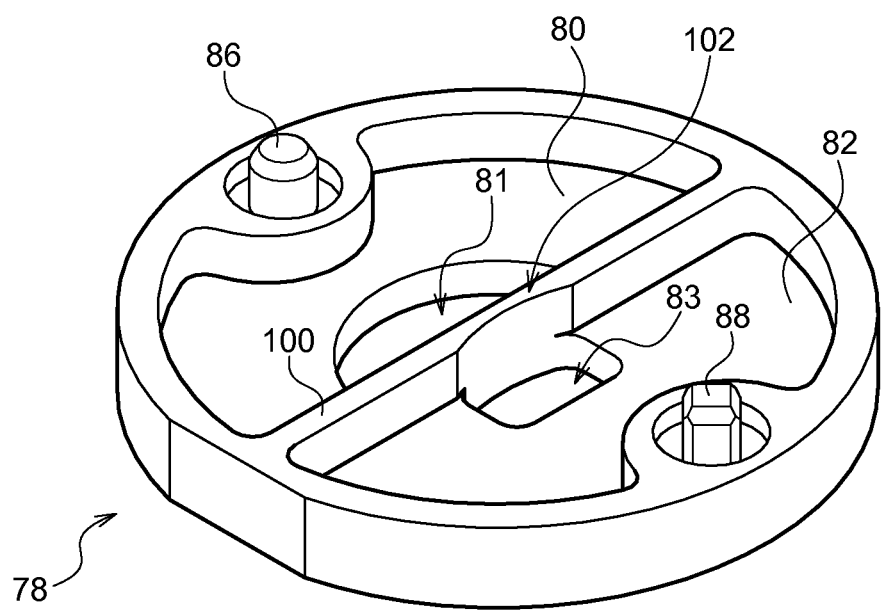
FIG. 13 is a perspective view of a first example of a light shielding member in which the diaphragm unit and the light shielding unit are formed integrally.

In this embodiment, the diaphragm units 80 and 82 and the light shielding unit 100 may be integrally formed as a light shielding member 78. That is, the diaphragm units 80 and 82 and the light shielding unit 100 (light shielding wall) have an integral structure. FIG. 13 is a perspective view showing a first example of the light shielding member 78 integrally formed in the above-described manner, and FIGS. 14A and 14B are a top view and a sectional view of the first example of the light shielding member 78.

Figure 14A:
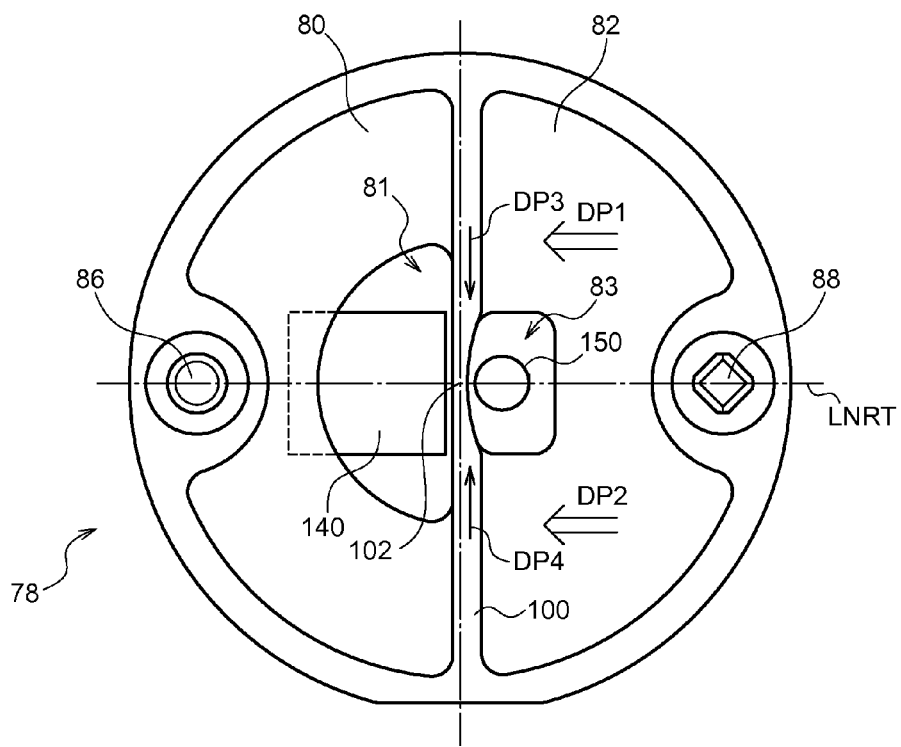
FIGS. 14A and 14B are a top view and a sectional view of the first example of the light shielding member in which the diaphragm unit and the light shielding unit are formed integrally.
Figure 14B:
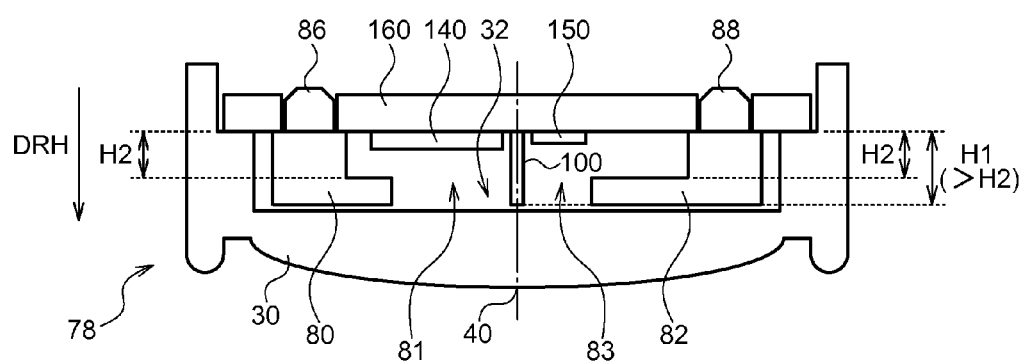

As shown in FIGS. 13 to 14B, in the light shielding member 78, the diaphragm unit 80 (first diaphragm unit) provided on the light receiving unit side and the diaphragm unit 82 (second diaphragm unit) provided on the light emitting unit side are formed. An opening 81 of the diaphragm on the light receiving unit side is formed corresponding to the diaphragm unit 80 on the light receiving unit side, and an opening 83 of the diaphragm on the light emitting unit side is formed corresponding to the diaphragm unit 82 on the light emitting unit side. The light shielding unit 100 is formed between the diaphragm units 80 and 82 integrally with the diaphragm units 80 and 82. For example, the light shielding member 78 has a shape of a bottomed tubular portion in which a bottom portion is formed at one side and the other end is opened, and the bottom portion of the bottomed tubular portion is formed as the diaphragm units 80 and 82. The openings 81 and 83 which function as an aperture are formed for the diaphragm units 80 and 82 in the bottom portion. The light shielding unit 100 is formed so as to bisect (divide) the region of the opening at the other end of the bottomed tubular portion.

As shown in FIGS. 13 and 14A, the thickness of the light shielding unit 100 becomes thin in the center portion 102. With this, it becomes possible to decrease the distance between the light receiving unit 140 and the light emitting unit 150, and to improve optical efficiency or performance.

The height of the light shielding unit 100 in the direction DRH orthogonal to the housing surface 22 (see FIGS. 3 and 4) of the biological information detection apparatus is referred to as H1, and the height of the lower surface which is the surface on the detection unit 130 side of each of the diaphragm units 80 and 82 is referred to as H2. The heights H1 and H2 are the height from a reference surface (for example, the substrate 160). In this case, as shown in FIG. 14B, the relationship H1>H2 is established. That is, the light shielding unit 100 becomes a light shielding wall which is formed to extend to a position higher than the lower surface of the diaphragm units 80 and 82. With this, it is possible to suppress a situation in which light from the light emitting unit 150 is reflected by the diaphragm units 80 and 82 and the like and enters the light receiving unit 140. That is, it becomes possible to eliminate the effect of direct reflected light of the light emitting unit 150, and to suppress degradation in reliability of measured data or the like.

As shown in FIG. 14B, the light shielding member 78 is attached toward the substrate 160 from the top (direction DRH) of the substrate 160 on which the light receiving unit 140 and the light emitting unit 150 are mounted. That is, the light shielding member 78 is attached such that the substrate 160 having the light receiving unit 140 and the light emitting unit 150 mounted thereon is inserted into the region of the opening at the other end of the bottomed tubular portion shape of the light shielding member 78. Protrusions 86 and 88 are formed in the light shielding member 78, and the protrusions 86 and 88 are engaged with hole portions formed in the substrate 160, whereby the light shielding member 78 is fixed to the substrate 160. Accordingly, for example, the diaphragm units 80 and 82, the light shielding unit 100, the light receiving unit 140, and the light emitting unit 150 are arranged at a position corresponding to the concave portion 32 on the rear side of the light transmitting member 30. In this case, the thickness of the light transmitting member 30 becomes thin in the portion of the concave portion 32. Accordingly, it is possible to reduce the length of the optical path which is the passing distance of light entering the light receiving unit 140 or light emitted from the light emitting unit 150 in the light transmitting member 30. Accordingly, the attenuation of light in the light transmitting member 30 is reduced, thereby improving the amount of transmitted light.

It is preferable that processing for improving optical efficiency or performance of the pulse wave sensor is performed on the diaphragm units 80 and 82 and the light shielding unit 100. For example, processing for roughening the surface (wall surface) of the diaphragm units 80 and 82 and the light shielding unit 100 is performed, thereby suppressing reflectance of light. Alternatively, the surface of the diaphragm units 80 and 82 and the light shielding unit 100 has a moth eye structure. For example, a rugged structure in a cycle of tens to hundreds of nm is formed on the surface to form a reflection prevention structure. Alternatively, the color of the surface of the diaphragm units 80 and 82 and the light shielding unit 100 is a predetermined color, such as black, thereby preventing irregular reflection. With this configuration, it is possible to effectively suppress a situation in which reflected light in the diaphragm units 80 and 82 and the light shielding unit 100 becomes stray light, and stray light becomes the noise component of measured data.

As described above, in order to improve optical efficiency or performance of the pulse wave sensor, it is preferable to minimize the distance between the light receiving unit 140 and the light emitting unit 150. For this reason, it is necessary that the light shielding unit 100 has a wall-thickness structure as thin as possible. In particular, in the center portion 102 (a region intersecting a line which connects the center position of the light receiving unit 140 and the center position of the light emitting unit 150) of the light shielding unit 100 of FIGS. 13 and 14A, the wall thickness of the light shielding unit 100 is thin.

However, in a single structure of the light shielding unit 100 whose wall thickness is thin, strength is lacking. For example, during traveling in which the pulsimeter is used or during cycling, since strong impact (for example, about 10 G) is applied to the apparatus, enough strength to cope with this impact is required.

Accordingly, in this embodiment, a method of forming the diaphragm units 80 and 82 and the light shielding unit 100 in an integral structure is utilized. That is, each of the diaphragm units 80 and 82 and the light shielding unit 100 is not realized by a single member, and as shown in FIG. 13, the light shielding member 78 in which the diaphragm units 80 and 82 and the light shielding unit 100 are integrally formed is used. With the light shielding member 78 integrally formed, even if the wall thickness of the light shielding unit 100 is thin, it becomes possible to ensure strength enough to bear with impact.

Since the diaphragm units 80 and 82 and the light shielding unit 100 are identical in terms of optical stabilization, the materials are readily shared. For example, it becomes easy to set the color of the surface of the diaphragm units 80 and 82 and the light shielding unit 100 in black so as to suppress the occurrence of irregular reflection.

The diaphragm units 80 and 82 and the light shielding unit 100 are integrally formed, thereby improving ease of assembling during component assembling and contributing to reduction in cost. For example, in FIG. 14B, the light shielding member 78 is inserted into the concave portion 32 of the light transmitting member 30, the protrusions 86 and 88 of the light shielding member 78 are fixed to be engaged with the substrate 160 having the light receiving unit 140 and the light emitting unit 150 mounted thereon, thereby completing assembling of the pulse wave sensor.

Taking the productivity of the apparatus into consideration, it is preferable to manufacture the light shielding member 78 by injection molding. However, if the wall thickness of the light shielding unit 100 is too thin, during injection molding, resin is not sufficiently filled in the portion of the light shielding unit 100.

Accordingly, in FIG. 14A, it is configured such that the area of the opening 83 of the diaphragm unit 82 on the light emitting unit side becomes smaller than the area of the opening 81 of the diaphragm unit 80 (first diaphragm unit) on the light receiving unit side.

In FIG. 14A, it is configured such that the wall thickness of the light shielding unit 100 is minimized on a line LNRT which connects the center of the light receiving unit 140 and the center of the light emitting unit 150. For example, the wall thickness becomes thin toward the center portion 102.

For example, if the area of the opening 83 on the light emitting unit side is small, the paths of DP1 and DP2 of FIG. 14A can be set in the path into which resin flows in injection molding. Resin flows into the path from DP1 to DP3 and the path from DP2 to DP4, whereby resin is sufficiently filled. For this reason, in the center portion 102 whose wall thickness is thin, the light shielding unit 100 can be formed of resin. For example, in general, the size of the light emitting unit 150 which is realized by an LED or the like is smaller than the size of the light receiving unit 140 which is realized by a semiconductor IC or the like of a photodiode. Accordingly, even if the area of the opening 83 on the light emitting unit side is small, there is no problem as much. The area of the opening 81 on the light receiving unit side is large, whereby it is possible to increase light receiving efficiency and to achieve improvement of the performance or the like of the biological information detection apparatus.

In this way, if the area of the opening 83 on the light emitting unit side is small to allow resin to easily flow, and the wall thickness in the center portion 102 of the light shielding unit 100 or the like is thin, it is possible to decrease the distance between the light receiving unit 140 and the light emitting unit 150. Accordingly, it is possible to improve optical efficiency or performance. That is, it becomes possible to prevent resin from being not sufficiently filled during injection molding and to achieve improvement of yield or the like while achieving both strength and optical efficiency or performance of the light shielding unit 100.

Figure 15:
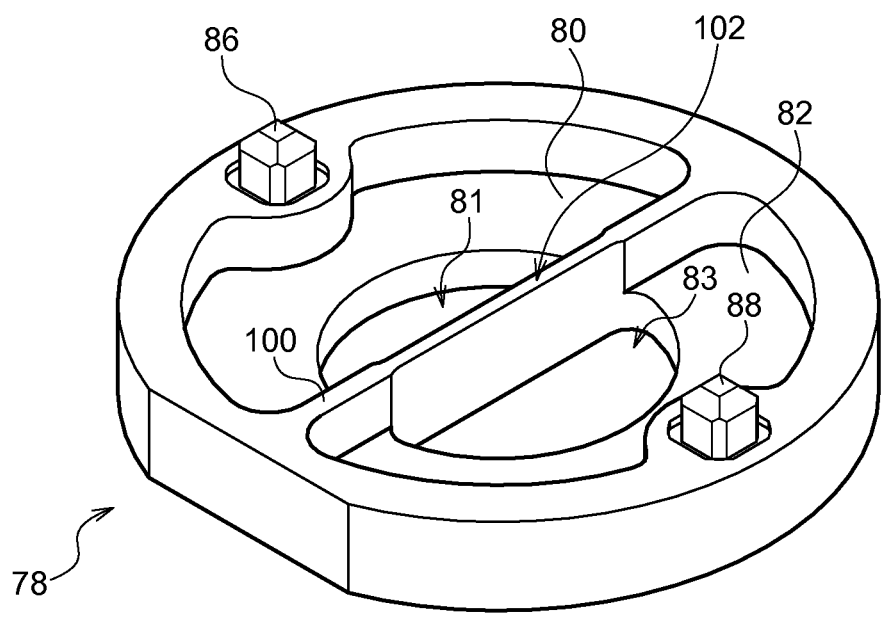
FIG. 15 is a perspective view of a second example of the light shielding member in which the diaphragm unit and the light shielding unit are formed integrally.
Figure 16A:
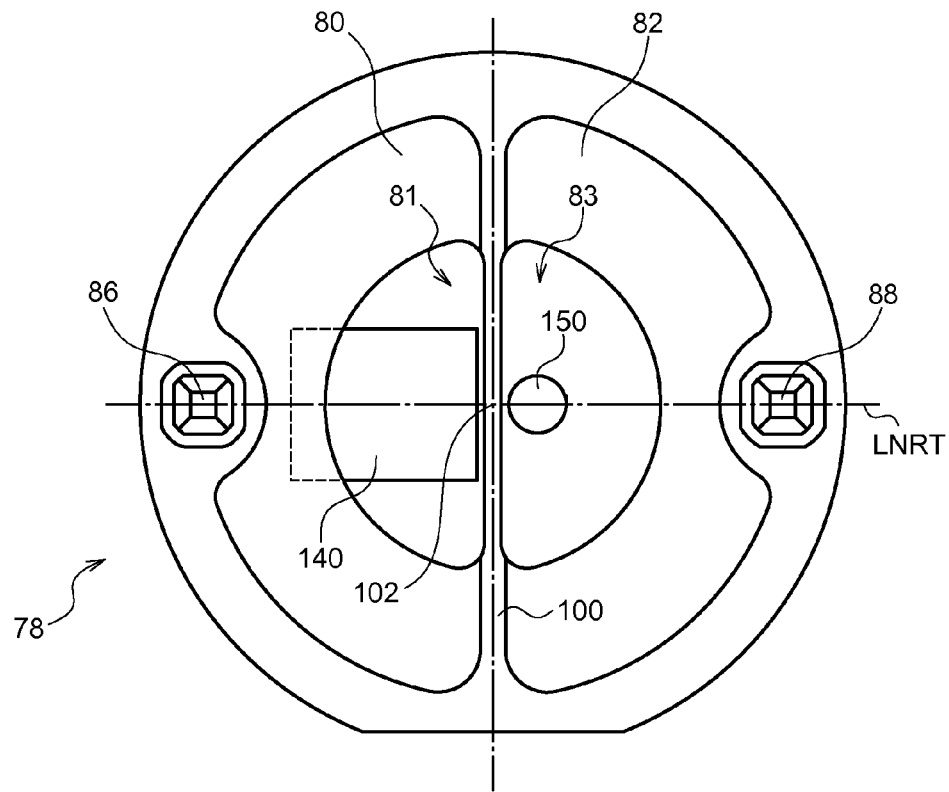
FIGS. 16A and 16B are a top view and a sectional view of the second example of the light shielding member in which the diaphragm unit and the light shielding unit are formed integrally.
Figure 16B:
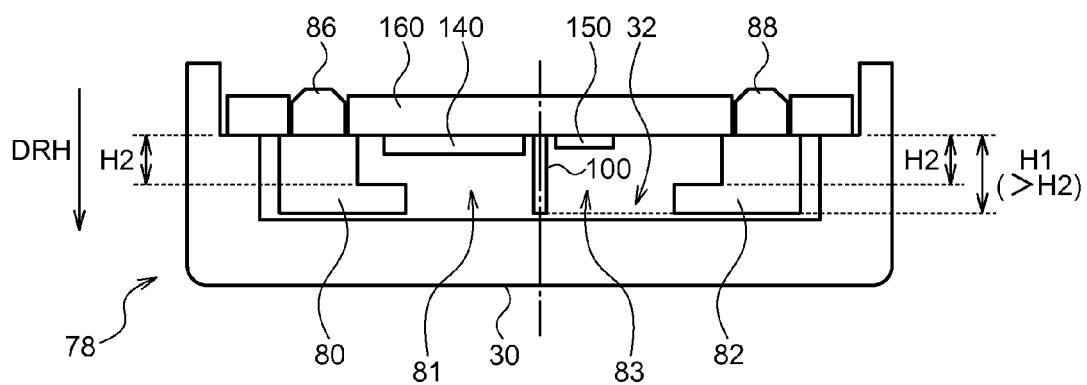

FIGS. 15, 16A and 16B are a perspective view, a top view, and a sectional view of a second example of the light shielding member 78 in which the diaphragm units 80 and 82 and the light shielding unit 100 are integrally formed. In the light shielding member 78 of the second example, as shown in FIG. 16A, the area of the opening 81 on the light receiving unit side becomes equal to the area of the opening 83 on the light emitting unit side. As shown in FIG. 16B, the light transmitting member 30 has no curved convex portion. In this way, as the structure or shape of the light shielding member 78, various modifications may be made.

4. Convex Portion of Light Transmitting Member

Figure 17A:
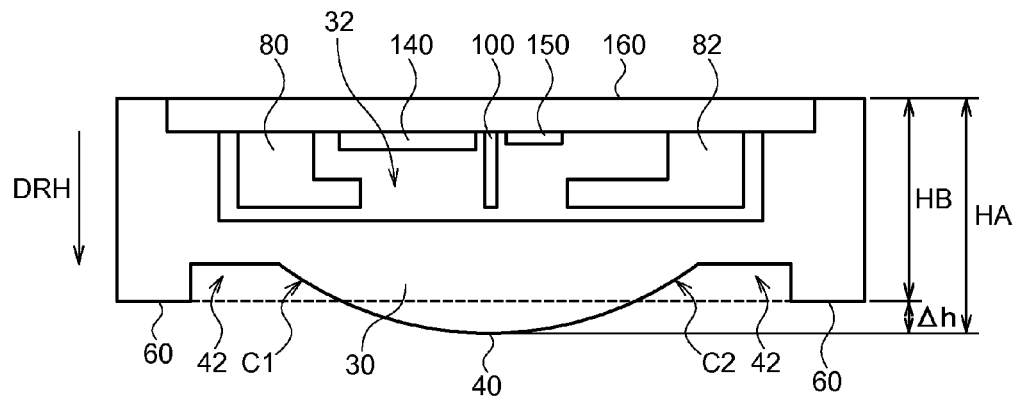
FIGS. 17A and 17B are explanatory views of a convex portion of the light transmitting member and a pressing force suppression unit.

As shown in FIG. 17A, in this embodiment, the light transmitting member 30 has the convex portion 40 which comes into contact with the subject and gives the pressing force when measuring the biological information of the subject.

As indicated by C1 and C2, the diaphragm units 80 and 82 shield light which passes through the marginal region of the convex portion 40. With this configuration, it is possible to suppress degradation in reliability of measured data or the like due to stray light at the locations where the contact state is unstable as indicated by C1 and C2.

In FIG. 17A, the pressing force suppression unit 60 is provided. The pressing force suppression unit 60 is provided so as to surround the convex portion 40 on the housing surface (the surface on the subject side) of the biological information detection apparatus, and suppresses the pressing force given to the subject by the convex portion 40. In FIGS. 3 and 4, the pressing force suppression unit 60 has a pressing force suppression surface which expands from the position of the convex portion 40 toward the second direction DR2 (the direction from the hand to the lower arm). Specifically, the pressing force suppression unit 60 is realized by a portion in a bank shape formed in the cover member 20.

In this case, for example, when the height of the convex portion 40 in the direction DRH orthogonal to the housing surface of the biological information detection apparatus is referred to as HA (for example, the height of the vertex of the curved shape of the convex portion 40), the height of the pressing force suppression unit 60 is referred to as HB (for example, the height at the highest location), and the value (the difference between the heights HA and HB) obtained by subtracting the height HB from the height HA is referred to as Δh, the relationship of Δh=HA−HB>0 is established. For example, the convex portion 40 protrudes from the pressing force suppression surface of the pressing force suppression unit 60 toward the subject such that Δh>0. That is, the convex portion 40 protrudes toward the subject by the amount corresponding to Δh from the pressing force suppression surface of the pressing force suppression unit 60.

In this way, the convex portion 40 having the relationship Δh>0 is provided, making it possible to give an initial pressing force for exceeding, for example, a vein vanishing point to the subject. The pressing force suppression unit 60 for suppressing the pressing force given to the subject by the convex portion 40 is provided, making it possible to minimize change in pressing force in the use range in which the biological information is measured by the biological information detection apparatus, and to achieve reduction in noise component or the like. The vein vanishing point is a point which, when the convex portion 40 is brought into contact with the subject and the pressing force gradually increases, a signal due to a vein superimposed on a pulse wave signal vanishes or becomes small without affecting pulse wave measurement.

Figure 17B:
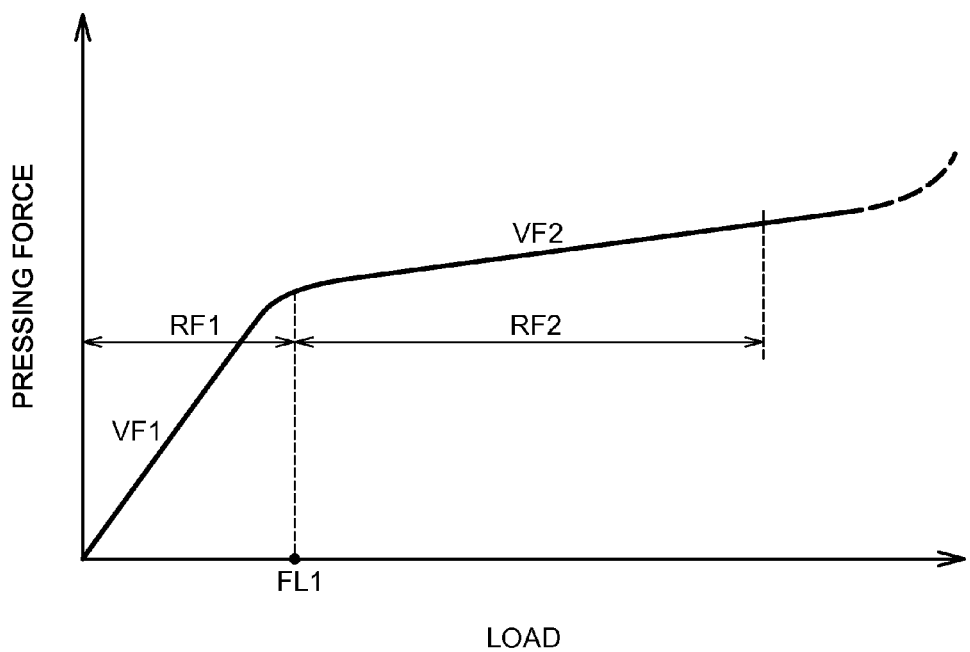

For example, in FIG. 17B, the horizontal axis represents a load which is generated by a load mechanism (a mechanism having an elastic member, such as spring or an extension/contraction portion, or a band) described referring to FIGS. 1B to 2C, and the vertical axis represents a pressing force (a pressure which is applied to a blood vessel) is given to the subject by the convex portion 40. The amount of change in pressing force of the convex portion 40 with respect to the load by the load mechanism generating the pressing force of the convex portion 40 is referred to as the amount of change in pressing force. The amount of change in pressing force corresponds to a slope of the characteristic of change in pressing force with respect to the load.

In this case, the pressing force suppression unit 60 suppresses the pressing force given to the subject by the convex portion 40 such that the amount VF2 of change in pressing force in a second load range RF2 in which the load of the load mechanism is greater than FL1 becomes smaller than the amount VF1 of change in pressing force in a first load range RF1 in which the load of the load mechanism becomes 0 to FL1. That is, in the first load range RF1 as an initial pressing force range, the amount VF1 of change in pressing force increases, and in the second load range RF2 as the use range of the biological information detection apparatus, the amount VF2 of change in pressing force decreases.

That is, in the first load range RF1, the amount VF1 of change in pressing force increases, thereby increasing the slope of the characteristic of change in pressing force with respect to the load. The pressing force having a large slope of the change characteristic is realized by Δh corresponding to the amount of protrusion of the convex portion 40. That is, the convex portion 40 having the relationship Δh>0 is provided, whereby, even when the load by the load mechanism is small, it becomes possible to give the initial pressing force necessary for exceeding the vein vanishing point to the subject.

In the second load range RF2, since the amount VF2 of change in pressing force is small, it is possible to decrease the slope of the characteristic of change in pressing force with respect to the load. The pressing force having a small slope of the change characteristic is realized by pressing force suppression by the pressing force suppression unit 60. That is, the pressing force given to the subject by the convex portion 40 is suppressed by the pressing force suppression unit 60, whereby, in the use range of the biological information detection apparatus, even when there is change in load or the like, it becomes possible to minimize change in pressing force. Therefore, reduction in the noise component or the like is achieved.

In this way, an optimum pressing force (for example, about 16 kPa) is given to the subject, thereby increasing a signal component (M) of the pulse wave sensor and reducing a noise component (N). The range of the pressing force for pulse wave measurement is set to a range corresponding to the second load range RF2, making it possible to minimize change in pressing force (for example, about ±4 kPa) and to reduce the noise component. The diaphragm units 80 and 82 or the light shielding unit 100 is used to reduce optical noise, making it possible to further reduce the noise component on the pulse wave detection signal.

Δh which represents the amount of protrusion of the convex portion 40 is an important parameter which specifies an optimum pressing force. That is, in order to constantly give the pressing force for exceeding the vein vanishing point, a certain amount of protrusion is required, and Δh should be set to a large value. However, if Δh becomes an excessive value, this may cause a decrease in the signal component of the pulse wave sensor or an increase in change in pressing force.

Accordingly, the minimum Δh is selected in a range in which the signal component of the pulse wave sensor can be sufficiently ensured, that is, in a range in which the optimum pressing force can be given. That is, in the range in which the optimum pressing force can be given, the smaller Δh, the lower the noise component can be suppressed.

Figure 18A:
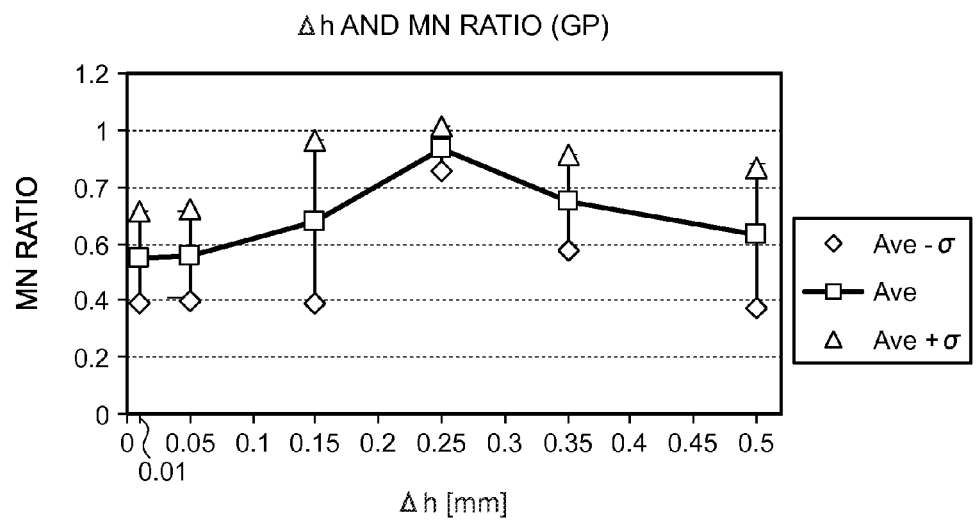
FIGS. 18A and 18B are diagrams showing the relationship between Δh and an MN ratio.
Figure 18B:
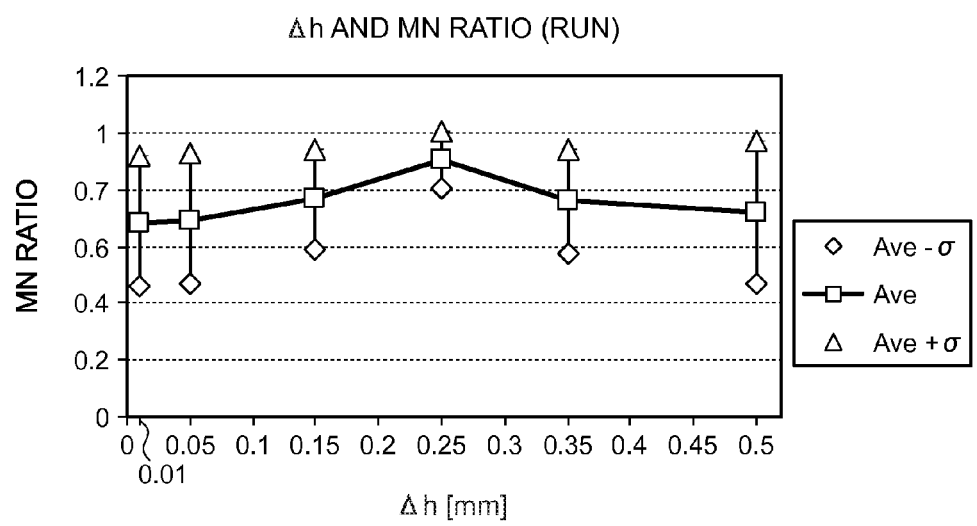

For example, FIG. 18A shows an example of a measured value which represents the relationship between Δh and the MN ratio (SN ratio) when the user performs a clasp and unclasp operation (GP). FIG. 18B shows an example of a measured value which represents the relationship between Δh and the MN ratio when the user performs a run operation (RUN). Here, the MN ratio corresponds to the ratio of the signal component (M) of the pulse wave sensor and the noise component (N).

From FIGS. 18A and 18B, it is understood that the range of Δh is preferably $0.01 \text{ mm} \leq \Delta h \leq 0.5 \text{ mm}$, and more preferably, $0.05 \text{ mm} \leq \Delta h \leq 0.35 \text{ mm}$. For example, when Δh=about 0.25 mm, it becomes possible to maximize the MN ratio. That is, in this way, Δh is set to a small value, whereby an increase in the noise component due to change in pressing force or the like is suppressed while giving the minimum pressing force for exceeding the vein vanishing point to the subject, making it possible to increase the MN ratio representing signal quality.

5. Overall Configuration of Biological Information Detection Apparatus

Figure 19:
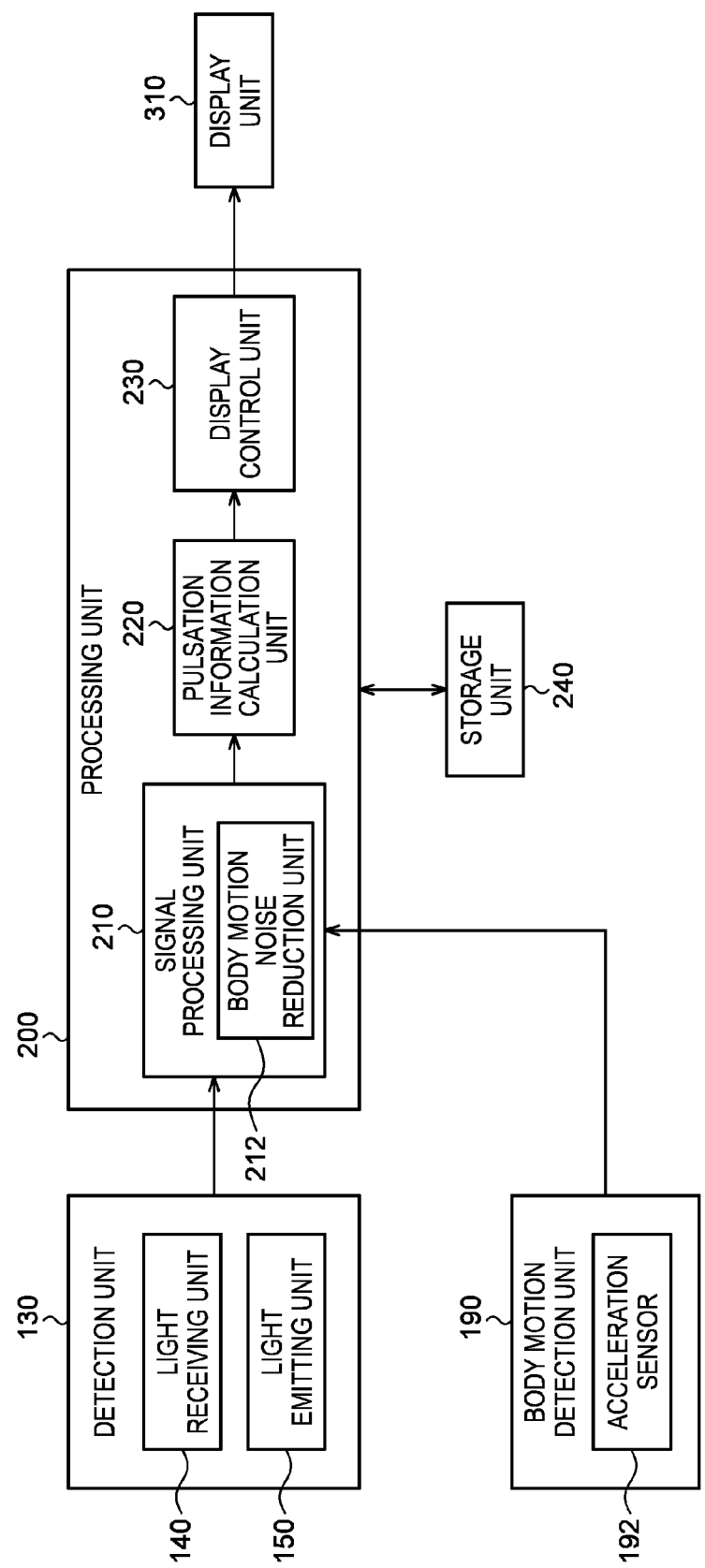
FIG. 19 is a functional block diagram showing an example of the overall configuration of the biological information detection apparatus.

FIG. 19 is a functional block diagram showing an example of the overall configuration of a biological information detection apparatus. The biological information detection apparatus of FIG. 19 includes a detection unit 130, a body motion detection unit 190, a processing unit 200, a storage unit 240, and a display unit 310. The biological information detection apparatus of this embodiment is not limited to the configuration of FIG. 19, various modifications in which some of the components are omitted and other components are added may be made.

The detection unit 130 detects biological information, such as a pulse wave, and includes a light receiving unit 140 and a light emitting unit 150. A pulse wave sensor (photoelectric sensor) is realized by the light receiving unit 140, the light emitting unit 150, and the like. The detection unit 130 outputs a signal detected by the pulse wave sensor as a pulse wave detection signal.

The body motion detection unit 190 outputs a body motion detection signal, which is a signal with change according to a body motion, on the basis of sensor information of various sensors. The body motion detection unit 190 includes, for example, an acceleration sensor 192, as a body motion sensor. The body motion detection unit 190 may have a pressure sensor or a gyro sensor as a body motion sensor.

The processing unit 200 performs various kinds of signal processing or control processing with the storage unit 240 as a work area, and can be realized by, for example, a processor, such as a CPU, or a logic circuit, such as an ASIC. The processing unit 200 includes a signal processing unit 210, a pulsation information calculation unit 220, and a display control unit 230.

The signal processing unit 210 performs various kinds of signal processing (filtering and the like), and performs signal processing on, for example, the pulse wave detection signal from the detection unit 130, the body motion detection signal from the body motion detection unit 190, or the like. For example, the signal processing unit 210 includes a body motion noise reduction unit 212. The body motion noise reduction unit 212 performs processing for reducing (eliminating) body motion noise as noise due to a body motion from the pulse wave detection signal on the basis of the body motion detection signal from the body motion detection unit 190. Specifically, for example, noise reduction processing using an adaptive filter or the like is performed.

The pulsation information calculation unit 220 performs calculation processing of pulsation information on the basis of a signal from the signal processing unit 210 or the like. The pulsation information is, for example, information, such as a pulse rate. Specifically, the pulsation information calculation unit 220 performs frequency analysis processing, such as FFT, on the pulse wave detection signal after the noise reduction processing in the body motion noise reduction unit 212 to obtain a spectrum, and performs processing for defining a representative frequency in the obtained spectrum as the frequency of heartbeat. A value 60 times the obtained frequency becomes a pulse rate (heart rate) which is generally used. The pulsation information is not limited to the pulse rate, and for example, various other kinds of information (for example, the frequency, cycle, or the like of heartbeat) representing the pulse rate may be used. Information representing the state of pulsation may be used, and for example, a value representing a blood volume may be used as the pulsation information.

The display control unit 230 performs display control for displaying various kinds of information or images on the display unit 310. For example, as shown in FIG. 1A, control is performed such that various kinds of information including the pulsation information, such as the pulse rate, time information, and the like, are displayed on the display unit 310. Instead of the display unit 310, a notice device which outputs light, sound, vibration, or the like stimulating perception of the user may be provided. As the notice device, for example, an LED, a buzzer, a vibrator, or the like may be assumed.

Although this embodiment has been described above in detail, it can be easily understood by those skilled in the art that many modifications may be made without departing from the new matter and effects of the invention in a substantive way. Accordingly, such modifications still fall within the scope of the invention. For example, in the specification or the drawings, there are some terms which are presented at least once together with other terms which have a broader meaning or the same meaning, and each of these terms can be replaced with the corresponding other term at any location in the specification and the drawings. The configuration and operation of the biological information detection apparatus are not limited to those described in this embodiment, and various modifications may be made.

What is claimed is:

1. A biological information detection apparatus comprising:
   a housing surface;
   a detection unit which has a light emitting unit which is configured to emit light to a subject and a light receiving unit configured to receive light from the subject, wherein the biological information detection apparatus is configured to be attached to the subject externally;
   a light transmitting member which is provided on the housing surface configured to be in contact with the subject of the biological information detection apparatus, transmits light from the light emitting unit and the subject, and configured to be placed adjacent to and comes into contact with skin of the subject while measuring biological information of the subject;
   a first diaphragm provided adjacent to or integral with the light transmitting member, wherein the first diaphragm is provided on light receiving unit side, wherein the first diaphragm is provided between the light transmitting member and the light receiving unit, between the light transmitting member and the subject, or inside the light transmitting member, wherein the first diaphragm includes an opening that is configured to narrows light from the subject in an optical path between the subject and the light receiving unit, wherein:
      an angle between a first line, which connects a first end portion of a light transmitting region of the light transmitting member and a first end portion of the light receiving unit as an end portion away from the first end portion of the light transmitting region out of two end portions of the light receiving unit, and an optical axis of the light receiving unit is θr,
      an angle between a second line, which connects the first end portion of the light receiving unit and an end portion on an opening side of the first diaphragm, and the optical axis is θa, and
      θa is less than θr; and
   a processing unit for processing an output of the detection unit.

2. The biological information detection apparatus according to claim 1, further comprising:
   a second diaphragm adjacent to the first diaphragm, wherein the second diaphragm is provided on light emitting unit side, the second diaphragm includes an opening that narrows light from the light emitting unit.

3. The biological information detection apparatus according to claim 2,
   wherein an area of the opening of the second diaphragm provided on the light emitting unit side is smaller than an area of the opening of the first diaphragm provided on the light receiving unit side.

4. The biological information detection apparatus according to claim 1, further comprising:

a light shielding unit which is provided between the light receiving unit and the light emitting unit.

5. The biological information detection apparatus according to claim 4, wherein:
a height of the light shielding unit in a direction orthogonal to the housing surface is H1, a height of a lower surface which is the surface of the first diaphragm on the detection unit side is H2, and H1 is greater than H2.

6. The biological information detection apparatus according to claim 4,
wherein the first diaphragm and the light shielding unit are formed integrally as a light shielding member.

7. The biological information detection apparatus according to claim 6,
wherein the light shielding member is attached to a substrate, on which the light receiving unit and the light emitting unit are mounted, from a top of the substrate.

8. The biological information detection apparatus according to claim 4,
wherein the light shielding unit is a light shielding wall which is formed to extend in a direction orthogonal to the housing surface.

9. The biological information detection apparatus according to claim 8,
wherein a width of the light shielding wall becomes thin toward a line connecting the light receiving unit and the light emitting unit.

10. The biological information detection apparatus according to claim 1, wherein the first diaphragm is located on a line, which connects the first end portion of the light transmitting region of the light transmitting member and a second end portion of the light receiving unit as an end portion close to the first end portion of the light transmitting region out of two end portions of the light receiving unit.

11. The biological information detection apparatus according to claim 2, wherein:
the angle between a line, which connects a second end portion of the light transmitting region of the light transmitting member and a first end portion of the light emitting unit as an end portion away from the second end portion of the light transmitting region out of two end portions of the light emitting unit, and the optical axis of the light emitting unit is θt,
the angle between a line, which connects the first end portion of the light emitting unit and an end portion on an opening side of the second diaphragm, and the optical axis is θb, and
θb is less than θt.

12. The biological information detection apparatus according to claim 2, wherein the first diaphragm is located on a line, which connects the first end portion of the light transmitting region of the light transmitting member and a first end portion of the light emitting unit as an end portion close to the first end portion of the light transmitting region out of two end portions of the light emitting unit, and the second diaphragm is located on a line, which connects a second end portion of the light transmitting region of the light transmitting member and a second end portion of the light emitting unit as an end portion close to the second end portion of the light transmitting region out of the two end portions of the light emitting unit.

13. The biological information detection apparatus according to claim 1,
wherein an area of a diaphragm region of the first diaphragm is smaller than an area of the light transmitting region of the light transmitting member.

14. The biological information detection apparatus according to claim 1,
wherein the light transmitting member has a convex portion which is configured to come into contact with the subject while measuring the biological information of the subject and gives a pressing force, and
the first diaphragm shields light passing through a marginal region of the convex portion.

15. The biological information detection apparatus according to claim 14, further comprising:
a pressing force suppression unit which is disposed in periphery of the convex portion, and is configured to suppress the pressing force given to the subject by the convex portion.

16. The biological information detection apparatus according to claim 15, wherein, an amount of change in the pressing force of the convex portion with respect to a load by a load mechanism generating the pressing force of the convex portion is defined as the amount of change in pressing force,
the pressing force suppression unit is configured to suppress the pressing force given to the subject by the convex portion such that the amount of change in pressing force in a second load range in which the load of the load mechanism is greater than FL1 becomes smaller than the amount of change in pressing force in a first load range in which the load of the load mechanism is 0 to FL1.

17. The biological information detection apparatus according to claim 1,
wherein a shape of a diaphragm region of the first diaphragm is similar to a shape of the light transmitting region of the light transmitting member.

18. The biological information detection apparatus according to claim 1,
wherein a pulse wave is detected as the biological information.

* * * * *